US009770278B2

(12) United States Patent
Lappin

(10) Patent No.: US 9,770,278 B2
(45) Date of Patent: Sep. 26, 2017

(54) DUAL TIP GUIDE WIRE

(71) Applicant: SONOMA ORTHOPEDIC PRODUCTS, INC., Santa Rosa, CA (US)

(72) Inventor: Kyle Lappin, Lake Zurich, IL (US)

(73) Assignee: ARTHREX, INC., Naples, FL (US)

(*) Notice: Subject to any disclaimer, the term of this patent is extended or adjusted under 35 U.S.C. 154(b) by 163 days.

(21) Appl. No.: 14/590,732

(22) Filed: Jan. 6, 2015

(65) Prior Publication Data
US 2015/0202413 A1    Jul. 23, 2015

Related U.S. Application Data

(60) Provisional application No. 61/928,792, filed on Jan. 17, 2014.

(51) Int. Cl.
*A61M 25/09* (2006.01)
*A61B 17/88* (2006.01)

(52) U.S. Cl.
CPC ..... *A61B 17/8897* (2013.01); *A61M 25/0905* (2013.01); *A61M 2025/09108* (2013.01); *Y10T 29/49826* (2015.01)

(58) Field of Classification Search
CPC . A61B 17/8897; A61B 17/72–17/7891; A61B 17/86–17/8635
USPC ........ 606/60, 62, 63, 64, 67, 68, 79, 80, 311
See application file for complete search history.

(56) References Cited

U.S. PATENT DOCUMENTS

| 958,127 A | 5/1910 | Hufrud |
| 1,169,635 A | 1/1916 | Grimes |
| 1,790,841 A | 2/1931 | Rosen |
| 2,502,267 A | 3/1950 | McPherson |
| 2,685,877 A | 8/1954 | Dobelle |
| 2,998,007 A | 8/1961 | Herzog |
| 3,118,444 A | 1/1964 | Serrato, Jr. |
| 3,441,017 A | 4/1969 | Kaessmann |
| 3,626,935 A | 12/1971 | Pollock et al. |
| 3,710,789 A | 1/1973 | Ersek |
| 3,717,146 A * | 2/1973 | Halloran ................ A61B 17/72 606/64 |
| 3,759,257 A | 9/1973 | Fischer et al. |
| 3,760,802 A | 9/1973 | Fischer et al. |
| 3,779,239 A | 12/1973 | Fischer et al. |
| 3,791,380 A | 2/1974 | Dawidowski |
| 3,805,775 A | 4/1974 | Fischer et al. |
| 3,846,846 A | 11/1974 | Fischer |
| 3,955,565 A | 5/1976 | Johnson, Jr. |
| 3,978,528 A | 9/1976 | Crep |

(Continued)

FOREIGN PATENT DOCUMENTS

| CA | 2561552 | 11/2005 |
| EP | 1582163 | 11/2003 |

(Continued)

OTHER PUBLICATIONS

US 6,030,385, 02/2000, Faccioli et al. (withdrawn)

(Continued)

*Primary Examiner* — Sean Dougherty
*Assistant Examiner* — Patrick Fernandes
(74) *Attorney, Agent, or Firm* — Carlson, Gaskey & Olds, P.C.

(57) ABSTRACT

Embodiments of a guide wire having a dual tip design and methods for using the guide wire.

20 Claims, 12 Drawing Sheets

(56) References Cited

U.S. PATENT DOCUMENTS

| | | |
|---|---|---|
| 3,986,504 A | 10/1976 | Avila |
| 4,007,528 A | 2/1977 | Shea et al. |
| 4,011,602 A | 3/1977 | Rybicki et al. |
| 4,016,874 A | 4/1977 | Maffei et al. |
| 4,050,464 A | 9/1977 | Hall |
| 4,064,567 A | 12/1977 | Burstein et al. |
| 4,065,816 A | 1/1978 | Sawyer |
| 4,091,806 A | 5/1978 | Aginsky |
| 4,146,022 A | 3/1979 | Johnson et al. |
| 4,164,794 A | 8/1979 | Spector et al. |
| 4,190,044 A | 2/1980 | Wood |
| D255,048 S | 5/1980 | Miller |
| 4,204,531 A | 5/1980 | Aginsky |
| 4,227,518 A | 10/1980 | Aginsky |
| 4,236,512 A | 12/1980 | Aginsky |
| 4,237,875 A | 12/1980 | Tennanini |
| 4,246,662 A | 1/1981 | Pastrick |
| 4,262,665 A | 4/1981 | Roalstad et al. |
| 4,275,717 A | 6/1981 | Bolesky |
| 4,293,962 A | 10/1981 | Fuson |
| 4,294,251 A | 10/1981 | Greenwald et al. |
| 4,312,336 A | 1/1982 | Danieletto et al. |
| 4,313,434 A | 2/1982 | Segal |
| 4,338,926 A | 7/1982 | Kummer et al. |
| 4,351,069 A | 9/1982 | Ballintyn et al. |
| 4,352,212 A | 10/1982 | Greene et al. |
| 4,353,358 A | 10/1982 | Emerson |
| 4,379,451 A | 4/1983 | Getscher |
| 4,409,974 A | 10/1983 | Freedland |
| 4,453,539 A | 6/1984 | Raftopoulos et al. |
| 4,457,301 A | 7/1984 | Walker |
| 4,459,708 A | 7/1984 | Buttazzoni |
| 4,462,394 A | 7/1984 | Jacobs |
| 4,467,794 A | 8/1984 | Maffei et al. |
| RE31,809 E | 1/1985 | Danieletto et al. |
| 4,492,226 A | 1/1985 | Belykh et al. |
| 4,503,847 A | 3/1985 | Mouradian |
| 4,519,100 A | 5/1985 | Wills et al. |
| 4,520,511 A | 6/1985 | Gianezio et al. |
| 4,522,200 A | 6/1985 | Stednitz |
| 4,541,423 A | 9/1985 | Barber |
| 4,552,136 A | 11/1985 | Kenna |
| 4,589,883 A | 5/1986 | Kenna |
| 4,590,930 A | 5/1986 | Kurth et al. |
| 4,604,997 A | 8/1986 | De Bastiani et al. |
| 4,621,627 A | 11/1986 | De Bastiani et al. |
| 4,622,959 A | 11/1986 | Marcus |
| 4,624,673 A | 11/1986 | Meyer |
| 4,628,920 A | 12/1986 | Mathys, Jr. et al. |
| 4,632,101 A | 12/1986 | Freedland |
| 4,643,177 A | 2/1987 | Sheppard et al. |
| 4,651,724 A | 3/1987 | Berentey et al. |
| 4,653,487 A | 3/1987 | Maale |
| 4,662,887 A | 5/1987 | Tuner et al. |
| 4,667,663 A | 5/1987 | Miyata |
| D290,399 S | 6/1987 | Kitchens |
| 4,681,590 A | 7/1987 | Tansey |
| 4,697,585 A | 10/1987 | Williams |
| 4,705,027 A | 11/1987 | Klaue |
| 4,705,032 A | 11/1987 | Keller |
| 4,721,103 A | 1/1988 | Freedland |
| 4,735,625 A | 4/1988 | Davidson |
| 4,753,657 A | 6/1988 | Lee et al. |
| 4,776,330 A | 10/1988 | Chapman et al. |
| 4,781,181 A | 11/1988 | Tanguy |
| 4,805,595 A | 2/1989 | Kanbara |
| 4,805,607 A | 2/1989 | Engelhardt et al. |
| 4,813,963 A | 3/1989 | Hori et al. |
| 4,817,591 A | 4/1989 | Klaue et al. |
| 4,827,919 A | 5/1989 | Barbarito et al. |
| 4,828,277 A | 5/1989 | De Bastiani et al. |
| 4,854,312 A | 8/1989 | Raftopoulos et al. |
| 4,858,602 A | 8/1989 | Seidel et al. |
| 4,862,883 A | 9/1989 | Freeland |
| 4,871,369 A | 10/1989 | Muller |
| 4,875,474 A | 10/1989 | Border |
| 4,875,475 A | 10/1989 | Comte et al. |
| 4,896,662 A | 1/1990 | Noble |
| 4,921,499 A | 5/1990 | Hoffman et al. |
| 4,927,424 A | 5/1990 | McConnell et al. |
| 4,932,969 A | 6/1990 | Frey et al. |
| 4,943,291 A | 7/1990 | Tanguy |
| 4,946,179 A | 8/1990 | De Bastiani et al. |
| 4,959,066 A | 9/1990 | Dunn et al. |
| 4,969,889 A | 11/1990 | Greig |
| 4,976,258 A | 12/1990 | Richter et al. |
| 4,978,349 A | 12/1990 | Frigg |
| 4,978,358 A | 12/1990 | Bobyn |
| 4,988,349 A | 1/1991 | Pennig |
| 5,002,547 A | 3/1991 | Poggie et al. |
| 5,002,580 A | 3/1991 | Noble et al. |
| 5,006,120 A | 4/1991 | Carter et al. |
| 5,013,314 A | 5/1991 | Firica et al. |
| 5,019,077 A | 5/1991 | De Bastiani et al. |
| 5,026,374 A | 6/1991 | Dezza et al. |
| 5,027,799 A | 7/1991 | Laico et al. |
| 5,030,222 A | 7/1991 | Calandruccio et al. |
| 5,034,012 A | 7/1991 | Frigg |
| 5,034,013 A | 7/1991 | Kyle et al. |
| 5,035,697 A | 7/1991 | Frigg |
| 5,037,423 A | 8/1991 | Kenna |
| 5,041,114 A | 8/1991 | Chapman et al. |
| 5,041,115 A | 8/1991 | Frigg et al. |
| 5,053,035 A | 10/1991 | McLaren |
| 5,057,103 A | 10/1991 | Davis |
| 5,062,854 A | 11/1991 | Noble et al. |
| 5,066,296 A | 11/1991 | Chapman et al. |
| 5,084,050 A | 1/1992 | Draenert |
| 5,092,892 A | 3/1992 | Ashby |
| 5,098,433 A | 3/1992 | Freedland |
| 5,100,404 A | 3/1992 | Hayes |
| 5,102,413 A | 4/1992 | Poddar |
| 5,108,404 A | 4/1992 | Scholten et al. |
| 5,112,333 A | 5/1992 | Fixel |
| 5,116,335 A | 5/1992 | Hannon et al. |
| 5,116,380 A | 5/1992 | Hewka et al. |
| 5,122,141 A | 6/1992 | Simpson et al. |
| 5,122,146 A | 6/1992 | Chapman et al. |
| 5,124,106 A | 6/1992 | Morr et al. |
| 5,147,408 A | 9/1992 | Noble et al. |
| 5,152,766 A | 10/1992 | Kirkley |
| 5,163,963 A | 11/1992 | Hewka et al. |
| 5,171,324 A | 12/1992 | Campana et al. |
| 5,176,681 A | 1/1993 | Lawes et al. |
| 5,178,621 A | 1/1993 | Cook et al. |
| 5,190,544 A | 3/1993 | Chapman et al. |
| 5,190,546 A | 3/1993 | Jervis |
| 5,192,281 A | 3/1993 | de la Caffiniere |
| 5,197,966 A | 3/1993 | Sommerkamp |
| 5,197,990 A | 3/1993 | Lawes et al. |
| 5,201,735 A | 4/1993 | Chapman et al. |
| 5,201,767 A | 4/1993 | Caldarise et al. |
| 5,211,664 A | 5/1993 | Tepic et al. |
| 5,217,049 A | 6/1993 | Forsyth |
| 5,263,955 A | 11/1993 | Baumgart et al. |
| 5,268,000 A | 12/1993 | Ottieri et al. |
| 5,281,224 A | 1/1994 | Faccioli et al. |
| 5,281,225 A | 1/1994 | Vicenzi |
| 5,292,322 A | 3/1994 | Faccioli et al. |
| 5,295,991 A | 3/1994 | Frigg |
| 5,303,718 A | 4/1994 | Krajicek |
| 5,314,489 A | 5/1994 | Hoffman et al. |
| 5,320,622 A | 6/1994 | Faccioli et al. |
| 5,320,623 A | 6/1994 | Pennig |
| 5,326,376 A | 7/1994 | Warner et al. |
| 5,334,184 A | 8/1994 | Bimman |
| 5,342,360 A | 8/1994 | Faccioli et al. |
| 5,342,362 A | 8/1994 | Kenyon et al. |
| 5,346,496 A | 9/1994 | Pennig |
| 5,350,379 A | 9/1994 | Spievack |
| 5,352,227 A | 10/1994 | O'Hara |
| 5,358,534 A | 10/1994 | Dudasik et al. |
| 5,364,398 A | 11/1994 | Chapman et al. |
| 5,368,594 A | 11/1994 | Martin et al. |

(56) References Cited

U.S. PATENT DOCUMENTS

| | | |
|---|---|---|
| 5,376,090 A | 12/1994 | Pennig |
| 5,376,123 A | 12/1994 | Klaue et al. |
| 5,380,328 A | 1/1995 | Morgan |
| 5,383,932 A | 1/1995 | Wilson et al. |
| 5,387,243 A | 2/1995 | Devanathan |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,417,695 A | 5/1995 | Axelson, Jr. |
| RE34,985 E | 6/1995 | Pennig |
| 5,423,848 A | 6/1995 | Washizuka et al. |
| 5,423,850 A | 6/1995 | Berger |
| 5,433,718 A | 7/1995 | Brinker |
| 5,433,720 A | 7/1995 | Faccioli et al. |
| 5,441,500 A | 8/1995 | Seidel et al. |
| 5,443,477 A | 8/1995 | Marin et al. |
| 5,445,642 A | 8/1995 | McNulty et al. |
| 5,454,813 A | 10/1995 | Lawes |
| 5,454,816 A | 10/1995 | Ashby |
| 5,458,599 A | 10/1995 | Adobbati |
| 5,458,651 A | 10/1995 | Lawes |
| 5,458,653 A | 10/1995 | Davidson |
| 5,468,242 A | 11/1995 | Reisberg |
| 5,472,444 A | 12/1995 | Huebner et al. |
| 5,478,341 A | 12/1995 | Cook et al. |
| 5,480,400 A | 1/1996 | Berger |
| 5,484,438 A | 1/1996 | Pennig |
| 5,484,446 A | 1/1996 | Burke et al. |
| 5,488,761 A | 2/1996 | Leone |
| 5,490,852 A | 2/1996 | Azer et al. |
| 5,505,734 A | 4/1996 | Caniggia et al. |
| 5,514,137 A | 5/1996 | Coutts |
| 5,516,335 A | 5/1996 | Kummer et al. |
| 5,520,695 A | 5/1996 | Luckman |
| 5,527,316 A | 6/1996 | Stone et al. |
| 5,531,748 A | 7/1996 | de la Caffiniere |
| 5,534,004 A | 7/1996 | Santangelo |
| 5,545,162 A | 8/1996 | Huebner |
| 5,549,610 A | 8/1996 | Russell et al. |
| 5,549,706 A | 8/1996 | McCarthy |
| 5,554,192 A | 9/1996 | Crowninshield |
| 5,556,433 A | 9/1996 | Gabriel et al. |
| 5,562,667 A | 10/1996 | Shuler et al. |
| 5,562,673 A | 10/1996 | Koblish et al. |
| 5,562,674 A | 10/1996 | Stalcup et al. |
| 5,562,675 A | 10/1996 | McNulty et al. |
| 5,569,249 A | 10/1996 | James et al. |
| 5,571,189 A | 11/1996 | Kuslich |
| 5,571,204 A | 11/1996 | Nies |
| 5,573,536 A | 11/1996 | Grosse et al. |
| 5,578,035 A | 11/1996 | Lin |
| 5,586,985 A | 12/1996 | Putnam et al. |
| 5,591,169 A | 1/1997 | Benoist |
| 5,591,196 A | 1/1997 | Marin et al. |
| 5,593,451 A | 1/1997 | Averill et al. |
| 5,593,452 A | 1/1997 | Higham et al. |
| 5,605,713 A | 2/1997 | Boltong |
| 5,607,431 A | 3/1997 | Dudasik et al. |
| 5,613,970 A | 3/1997 | Houston et al. |
| 5,618,286 A | 4/1997 | Brinker |
| 5,618,300 A | 4/1997 | Marin et al. |
| 5,620,449 A | 4/1997 | Faccioli et al. |
| 5,624,440 A | 4/1997 | Huebner et al. |
| 5,624,447 A | 4/1997 | Myers |
| 5,626,580 A | 5/1997 | Brosnahan |
| 5,643,258 A | 7/1997 | Robioneck et al. |
| 5,645,545 A | 7/1997 | Bryant |
| 5,645,599 A | 7/1997 | Samani |
| 5,658,283 A | 8/1997 | Huebner |
| 5,658,287 A | 8/1997 | Hofmann et al. |
| 5,658,292 A | 8/1997 | Axelson, Jr. |
| 5,658,293 A | 8/1997 | Vanlaningham |
| 5,658,351 A | 8/1997 | Dudasik et al. |
| 5,662,648 A | 9/1997 | Faccioli et al. |
| 5,662,649 A | 9/1997 | Huebner |
| 5,662,712 A | 9/1997 | Pathak et al. |
| 5,665,090 A | 9/1997 | Rockwood et al. |
| 5,665,091 A | 9/1997 | Noble et al. |
| 5,681,289 A | 10/1997 | Wilcox et al. |
| 5,681,316 A | 10/1997 | DeOrio et al. |
| 5,681,318 A | 10/1997 | Pennig et al. |
| 5,683,389 A | 11/1997 | Orsak |
| 5,683,460 A | 11/1997 | Persoons |
| 5,688,271 A | 11/1997 | Faccioli et al. |
| 5,688,279 A | 11/1997 | McNulty et al. |
| 5,690,634 A | 11/1997 | Muller et al. |
| 5,693,047 A | 12/1997 | Meyers et al. |
| 5,693,048 A | 12/1997 | Stalcup et al. |
| 5,695,729 A | 12/1997 | Chow et al. |
| 5,697,930 A | 12/1997 | Itoman et al. |
| 5,702,215 A | 12/1997 | Li |
| 5,702,481 A | 12/1997 | Lin |
| 5,702,487 A | 12/1997 | Averill et al. |
| 5,707,370 A | 1/1998 | Berki et al. |
| 5,718,704 A | 2/1998 | Medoff |
| 5,725,595 A | 3/1998 | Gustilo |
| 5,728,096 A | 3/1998 | Faccioli et al. |
| 5,741,256 A | 4/1998 | Bresina |
| 5,741,266 A | 4/1998 | Moran et al. |
| 5,749,872 A | 5/1998 | Kyle et al. |
| 5,749,880 A | 5/1998 | Banas et al. |
| 5,759,184 A | 6/1998 | Santangelo |
| 5,766,174 A | 6/1998 | Perry |
| 5,766,176 A | 6/1998 | Duncan |
| 5,766,178 A | 6/1998 | Michielli et al. |
| 5,766,179 A | 6/1998 | Faccioli et al. |
| 5,766,180 A | 6/1998 | Winquist |
| 5,772,662 A | 6/1998 | Chapman et al. |
| 5,772,663 A | 6/1998 | Whiteside et al. |
| 5,776,194 A | 7/1998 | Mikol et al. |
| 5,776,204 A | 7/1998 | Noble et al. |
| 5,779,703 A | 7/1998 | Benoist |
| 5,779,705 A | 7/1998 | Matthews |
| 5,782,921 A | 7/1998 | Colleran et al. |
| 5,785,057 A | 7/1998 | Fischer |
| 5,788,703 A | 8/1998 | Mittelmeier et al. |
| 5,807,241 A | 9/1998 | Heimberger |
| 5,810,750 A | 9/1998 | Buser |
| 5,810,820 A | 9/1998 | Santori et al. |
| 5,810,826 A | 9/1998 | Åkerfeldt et al. |
| 5,810,830 A | 9/1998 | Noble et al. |
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,827,289 A | 10/1998 | Reiley et al. |
| 5,829,081 A | 11/1998 | Pearce |
| 5,836,949 A | 11/1998 | Campbell, Jr. et al. |
| 5,837,909 A | 11/1998 | Bill et al. |
| 5,849,004 A | 12/1998 | Bramlet |
| 5,849,014 A | 12/1998 | Mastrorio et al. |
| 5,849,035 A | 12/1998 | Pathak et al. |
| 5,855,581 A | 1/1999 | Koblish et al. |
| 5,858,020 A | 1/1999 | Johnson et al. |
| 5,863,295 A | 1/1999 | Averill et al. |
| 5,876,459 A | 3/1999 | Powell |
| 5,879,352 A | 3/1999 | Filoso et al. |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,906,210 A | 5/1999 | Herbert |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |

(56) References Cited

U.S. PATENT DOCUMENTS

| | | |
|---|---|---|
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,951,561 A | 9/1999 | Pepper et al. |
| 5,954,722 A | 9/1999 | Bono |
| 5,954,728 A | 9/1999 | Heller et al. |
| 5,961,553 A | 10/1999 | Coty et al. |
| 5,964,770 A | 10/1999 | Flomenblit et al. |
| 5,968,047 A | 10/1999 | Reed |
| 5,971,986 A | 10/1999 | Santori et al. |
| 5,976,134 A | 11/1999 | Huebner |
| 5,976,139 A | 11/1999 | Bramlet |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,018,094 A | 1/2000 | Fox |
| 6,019,761 A | 2/2000 | Gustilo |
| 6,019,762 A | 2/2000 | Cole |
| 6,020,396 A | 2/2000 | Jacobs |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |
| 6,039,742 A | 3/2000 | Krettek et al. |
| 6,045,556 A | 4/2000 | Cohen |
| 6,053,922 A | 4/2000 | Krause et al. |
| 6,056,756 A | 5/2000 | Eng et al. |
| 6,074,392 A | 6/2000 | Durham |
| 6,077,264 A | 6/2000 | Chemello |
| 6,080,159 A | 6/2000 | Vichard |
| 6,083,522 A | 7/2000 | Chu et al. |
| 6,093,209 A | 7/2000 | Sanders |
| 6,096,040 A | 8/2000 | Esser |
| 6,102,911 A | 8/2000 | Faccioli et al. |
| 6,106,528 A | 8/2000 | Durham et al. |
| 6,120,504 A | 9/2000 | Brumback et al. |
| 6,120,509 A | 9/2000 | Wheeler |
| 6,126,661 A | 10/2000 | Faccioli et al. |
| 6,126,691 A | 10/2000 | Kasra et al. |
| 6,127,597 A | 10/2000 | Beyar et al. |
| 6,129,756 A | 10/2000 | Kugler et al. |
| 6,129,762 A | 10/2000 | Li |
| 6,139,583 A | 10/2000 | Johnson |
| 6,143,012 A | 11/2000 | Gausepohl |
| 6,143,033 A | 11/2000 | Paul et al. |
| 6,162,223 A | 12/2000 | Orsak et al. |
| 6,162,226 A | 12/2000 | DeCarlo et al. |
| 6,168,595 B1 | 1/2001 | Durham et al. |
| 6,168,632 B1 | 1/2001 | Moser et al. |
| 6,171,309 B1 | 1/2001 | Huebner |
| 6,176,871 B1 | 1/2001 | Pathak et al. |
| 6,179,839 B1 | 1/2001 | Weiss et al. |
| 6,179,842 B1 | 1/2001 | Spotomo et al. |
| 6,183,470 B1 | 2/2001 | Booth, Jr. et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,456 B1 | 8/2001 | Scribner et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,309,396 B1 | 10/2001 | Ritland |
| 6,319,253 B1 | 11/2001 | Ackeret et al. |
| 6,325,830 B1 | 12/2001 | Mastrorio et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,044 B1 | 3/2002 | Hair |
| 6,355,069 B1 | 3/2002 | DeCarlo et al. |
| 6,358,250 B1 | 3/2002 | Orbay |
| 6,358,283 B1 | 3/2002 | Hogfors et al. |
| 6,364,824 B1 | 4/2002 | Fitzsimmons |
| 6,364,882 B1 | 4/2002 | Orbay |
| 6,364,909 B1 | 4/2002 | McGee |
| 6,379,359 B1 | 4/2002 | Dahners |
| 6,379,360 B1 | 4/2002 | Ackeret et al. |
| 6,383,188 B2 | 5/2002 | Kuslich et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,083 B2 | 7/2002 | Reiley et al. |
| 6,423,096 B1 | 7/2002 | Musset et al. |
| 6,425,923 B1 | 7/2002 | Stalcup et al. |
| 6,436,148 B1 | 8/2002 | DeCarlo, Jr. et al. |
| 6,440,135 B2 | 8/2002 | Orbay et al. |
| 6,443,954 B1 | 9/2002 | Bramlet et al. |
| 6,443,992 B2 | 9/2002 | Lubinus |
| 6,447,513 B1 | 9/2002 | Griggs |
| 6,447,514 B1 | 9/2002 | Stalcup et al. |
| 6,447,515 B1 | 9/2002 | Meldrum |
| 6,447,518 B1 | 9/2002 | Krause et al. |
| 6,461,358 B1 | 10/2002 | Faccioli |
| 6,461,360 B1 | 10/2002 | Adam |
| 6,468,278 B1 | 10/2002 | Muckter |
| 6,488,684 B2 | 12/2002 | Bramlet et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B2 | 1/2003 | von Hoffmann et al. |
| 6,520,994 B2 | 2/2003 | Nogarin |
| 6,524,313 B1 | 2/2003 | Fassier et al. |
| 6,527,775 B1 | 3/2003 | Warburton |
| 6,530,925 B2 | 3/2003 | Boudard et al. |
| 6,533,788 B2 | 3/2003 | Orbay |
| 6,537,275 B2 | 3/2003 | Venturini et al. |
| 6,540,752 B1 | 4/2003 | Hicken et al. |
| 6,544,265 B2 | 4/2003 | Lieberman |
| 6,551,319 B2 | 4/2003 | Lieberman |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 | 5/2003 | Bartsch et al. |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Marin et al. |
| 6,582,453 B1 | 6/2003 | Tran et al. |
| 6,592,578 B2 | 7/2003 | Henniges et al. |
| 6,607,531 B2 | 8/2003 | Frigg |

(56) References Cited

U.S. PATENT DOCUMENTS

| | | |
|---|---|---|
| 6,613,052 B1 | 9/2003 | Kinnett |
| 6,616,667 B1 | 9/2003 | Steiger et al. |
| 6,616,742 B2 | 9/2003 | Lin et al. |
| 6,620,197 B2 | 9/2003 | Maroney |
| 6,623,487 B1 | 9/2003 | Goshert |
| 6,629,976 B1 | 10/2003 | Gnos et al. |
| 6,632,224 B2 | 10/2003 | Cachia et al. |
| 6,632,235 B2 | 10/2003 | Weikel et al. |
| 6,641,596 B1 | 11/2003 | Uzardi |
| 6,648,889 B2 | 11/2003 | Bramlet et al. |
| 6,648,890 B2 | 11/2003 | Culbert et al. |
| 6,648,893 B2 | 11/2003 | Dudasik |
| 6,652,529 B2 | 11/2003 | Swanson |
| 6,652,591 B2 | 11/2003 | Serbousek et al. |
| 6,656,189 B1 | 12/2003 | Wilson et al. |
| 6,663,647 B2 | 12/2003 | Reiley et al. |
| 6,679,890 B2 | 1/2004 | Margulies et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,692,530 B2 | 2/2004 | Doubler et al. |
| 6,694,667 B2 | 2/2004 | Davis |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,719,793 B2 | 4/2004 | McGee |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,749,614 B2 | 6/2004 | Teitelbaum et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,790,210 B1 | 9/2004 | Cragg et al. |
| 6,793,655 B2 | 9/2004 | Orsak |
| 6,793,659 B2 | 9/2004 | Putnam |
| 6,808,527 B2 | 10/2004 | Lower et al. |
| 6,821,277 B2 | 11/2004 | Teitelbaum |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,875,212 B2 | 4/2005 | Shaolian et al. |
| 6,887,243 B2 | 5/2005 | Culbert |
| 6,887,271 B2 | 5/2005 | Justin et al. |
| 6,887,276 B2 | 5/2005 | Gerbec et al. |
| 6,890,333 B2 | 5/2005 | von Hoffmann et al. |
| 6,893,444 B2 | 5/2005 | Orbay |
| 6,899,713 B2 | 5/2005 | Shaolian et al. |
| 6,899,719 B2 | 5/2005 | Reiley et al. |
| 6,902,583 B2 | 6/2005 | Gerbec et al. |
| 6,908,465 B2 | 6/2005 | von Hoffmann et al. |
| 6,916,323 B2 | 7/2005 | Kitchens |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,981,981 B2 | 1/2006 | Reiley et al. |
| 6,986,771 B2 | 1/2006 | Paul et al. |
| 6,999,819 B2 | 2/2006 | Swoyer et al. |
| 7,001,386 B2 | 2/2006 | Sohngen et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 | 5/2006 | Levy et al. |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,081,119 B2 | 7/2006 | Stihl |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 | 12/2009 | Woll et al. |
| 7,846,162 B2 | 12/2010 | Nelson et al. |
| 7,909,825 B2 | 3/2011 | Saravia et al. |
| 7,914,533 B2 | 3/2011 | Nelson et al. |
| 7,942,875 B2 | 5/2011 | Nelson et al. |
| 8,128,627 B2 | 3/2012 | Justin et al. |
| 8,287,539 B2 | 10/2012 | Nelson et al. |
| 8,287,541 B2 | 10/2012 | Nelson et al. |
| 8,430,879 B2 | 4/2013 | Stoneburner et al. |
| 8,439,917 B2 | 5/2013 | Nelson et al. |
| 8,496,658 B2 | 7/2013 | Stoneburner et al. |
| 8,568,413 B2 | 10/2013 | Mazur et al. |
| 8,961,516 B2 | 2/2015 | Nelson et al. |
| 9,060,820 B2 | 6/2015 | Nelson et al. |
| 9,155,574 B2 | 10/2015 | Saravia et al. |
| 2001/0011174 A1 | 8/2001 | Reiley et al. |
| 2001/0034526 A1 | 10/2001 | Kuslich et al. |
| 2001/0049531 A1 | 12/2001 | Reiley et al. |
| 2002/0004685 A1 | 1/2002 | White |
| 2002/0029041 A1 | 3/2002 | Hover et al. |
| 2002/0032444 A1 | 3/2002 | Mische |
| 2002/0041896 A1 | 4/2002 | Straub et al. |
| 2002/0068939 A1 | 6/2002 | Levy et al. |

(56) References Cited

U.S. PATENT DOCUMENTS

| | | |
|---|---|---|
| 2002/0068981 A1 | 6/2002 | Hajianpour |
| 2002/0095214 A1 | 7/2002 | Hyde, Jr. |
| 2002/0099385 A1 | 7/2002 | Ralph et al. |
| 2002/0103488 A1 | 8/2002 | Lower et al. |
| 2002/0143344 A1 | 10/2002 | Taylor |
| 2002/0161369 A1 | 10/2002 | Bramlet et al. |
| 2002/0165544 A1 | 11/2002 | Perren et al. |
| 2002/0173792 A1 | 11/2002 | Sevems et al. |
| 2002/0177866 A1 | 11/2002 | Weikel et al. |
| 2002/0188297 A1 | 12/2002 | Dakin et al. |
| 2002/0198526 A1 | 12/2002 | Shaolian et al. |
| 2003/0032960 A1 | 2/2003 | Dudasik |
| 2003/0040752 A1 | 2/2003 | Kitchens |
| 2003/0045919 A1 | 3/2003 | Swoyer et al. |
| 2003/0073999 A1 | 4/2003 | Putnam |
| 2003/0074075 A1 | 4/2003 | Thomas, Jr. et al. |
| 2003/0078581 A1 | 4/2003 | Frei et al. |
| 2003/0078669 A1 | 4/2003 | Martin et al. |
| 2003/0097136 A1 | 5/2003 | Hajianpour |
| 2003/0109932 A1 | 6/2003 | Keynan |
| 2003/0130660 A1 | 7/2003 | Levy et al. |
| 2003/0130664 A1 | 7/2003 | Boucher et al. |
| 2003/0139802 A1 | 7/2003 | Wulfman et al. |
| 2003/0181918 A1 | 9/2003 | Smothers et al. |
| 2003/0216738 A1 | 11/2003 | Azar |
| 2003/0236529 A1 | 12/2003 | Shluzas et al. |
| 2004/0006341 A1 | 1/2004 | Shaolian et al. |
| 2004/0010263 A1 | 1/2004 | Boucher et al. |
| 2004/0064143 A1* | 4/2004 | Hicken ............... A61B 17/885 606/90 |
| 2004/0098017 A1 | 5/2004 | Saab et al. |
| 2004/0098134 A1 | 5/2004 | Meulink |
| 2004/0133204 A1 | 7/2004 | Davies |
| 2004/0133280 A1 | 7/2004 | Trieu |
| 2004/0153114 A1 | 8/2004 | Reiley et al. |
| 2004/0153115 A1 | 8/2004 | Reiley et al. |
| 2004/0167519 A1* | 8/2004 | Weiner ............... A61B 17/8665 606/60 |
| 2004/0167561 A1 | 8/2004 | Boucher et al. |
| 2004/0193255 A1 | 9/2004 | Shanley et al. |
| 2004/0193267 A1 | 9/2004 | Jones et al. |
| 2004/0213825 A1 | 10/2004 | Levy |
| 2004/0214311 A1 | 10/2004 | Levy |
| 2004/0215193 A1 | 10/2004 | Shaolian et al. |
| 2004/0230193 A1 | 11/2004 | Cheung et al. |
| 2004/0236327 A1 | 11/2004 | Paul et al. |
| 2004/0260398 A1 | 12/2004 | Kelman |
| 2004/0267269 A1 | 12/2004 | Middleton et al. |
| 2004/0267271 A9 | 12/2004 | Scribner et al. |
| 2005/0015154 A1 | 1/2005 | Lindsey et al. |
| 2005/0027294 A1 | 2/2005 | Woll |
| 2005/0027301 A1 | 2/2005 | Stihl |
| 2005/0043737 A1 | 2/2005 | Reiley et al. |
| 2005/0043757 A1 | 2/2005 | Arad et al. |
| 2005/0047892 A1 | 3/2005 | Bremner |
| 2005/0055023 A1 | 3/2005 | Sohngen et al. |
| 2005/0055024 A1 | 3/2005 | James et al. |
| 2005/0080425 A1 | 4/2005 | Bhatnagar et al. |
| 2005/0090852 A1 | 4/2005 | Layne et al. |
| 2005/0107883 A1 | 5/2005 | Goodfried et al. |
| 2005/0119662 A1 | 6/2005 | Reiley et al. |
| 2005/0131386 A1 | 6/2005 | Freeman et al. |
| 2005/0143827 A1 | 6/2005 | Globerman et al. |
| 2005/0149022 A1 | 7/2005 | Shaolian et al. |
| 2005/0149024 A1 | 7/2005 | Ferrante et al. |
| 2005/0149025 A1 | 7/2005 | Ferrante et al. |
| 2005/0159749 A1 | 7/2005 | Levy et al. |
| 2005/0165395 A1 | 7/2005 | Orbay et al. |
| 2005/0171552 A1 | 8/2005 | Johnson et al. |
| 2005/0171563 A1 | 8/2005 | Heinrich et al. |
| 2005/0177158 A1 | 8/2005 | Doubler et al. |
| 2005/0203510 A1 | 9/2005 | Sohngen et al. |
| 2005/0209595 A1 | 9/2005 | Karmon |
| 2005/0216007 A1 | 9/2005 | Woll et al. |
| 2005/0228391 A1 | 10/2005 | Levy et al. |
| 2005/0234453 A1 | 10/2005 | Shaolian et al. |
| 2005/0234559 A1 | 10/2005 | Fernandez et al. |
| 2005/0251140 A1 | 11/2005 | Shaolian et al. |
| 2005/0261781 A1 | 11/2005 | Sennett et al. |
| 2005/0267481 A1 | 12/2005 | Carl et al. |
| 2005/0267483 A1 | 12/2005 | Middleton |
| 2005/0267586 A1 | 12/2005 | Sidebotham |
| 2005/0277940 A1* | 12/2005 | Neff ............... A61B 17/7225 606/916 |
| 2005/0283250 A1 | 12/2005 | Coon et al. |
| 2005/0288678 A1 | 12/2005 | Reiley et al. |
| 2006/0004465 A1 | 1/2006 | Bergin et al. |
| 2006/0015101 A1 | 1/2006 | Warburton et al. |
| 2006/0015123 A1 | 1/2006 | Fencl et al. |
| 2006/0030945 A1 | 2/2006 | Wright |
| 2006/0036248 A1 | 2/2006 | Ferrante |
| 2006/0052788 A1 | 3/2006 | Thelen et al. |
| 2006/0064094 A1 | 3/2006 | Levy et al. |
| 2006/0084997 A1 | 4/2006 | Dejardin |
| 2006/0084998 A1 | 4/2006 | Levy et al. |
| 2006/0122601 A1 | 6/2006 | Tandon |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264950 A1 | 11/2006 | Nelson et al. |
| 2006/0264951 A1 | 11/2006 | Nelson et al. |
| 2007/0123878 A1 | 5/2007 | Shaver et al. |
| 2007/0142916 A1 | 6/2007 | Olson et al. |
| 2007/0260257 A1 | 11/2007 | Phan |
| 2008/0077154 A1 | 3/2008 | Edwards et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0221620 A1 | 9/2008 | Krause et al. |
| 2008/0234678 A1 | 9/2008 | Gutierrez et al. |
| 2008/0243132 A1 | 10/2008 | Tipirneni et al. |
| 2008/0255560 A1 | 10/2008 | Myers et al. |
| 2008/0262495 A1 | 10/2008 | Coati et al. |
| 2008/0269751 A1 | 10/2008 | Matityahu |
| 2008/0269776 A1 | 10/2008 | Justin |
| 2008/0287951 A1 | 11/2008 | Stoneburner et al. |
| 2009/0018542 A1 | 1/2009 | Saravia et al. |
| 2009/0182336 A1 | 7/2009 | Brenzel et al. |
| 2009/0187116 A1 | 7/2009 | Noishiki et al. |
| 2009/0216232 A1 | 8/2009 | Buford et al. |
| 2009/0228007 A1 | 9/2009 | Justin et al. |
| 2009/0228008 A1 | 9/2009 | Justin et al. |
| 2010/0023010 A1 | 1/2010 | Nelson et al. |
| 2010/0094347 A1 | 4/2010 | Nelson et al. |
| 2010/0121326 A1* | 5/2010 | Woll ............... A61B 17/7225 606/63 |
| 2011/0087227 A1 | 4/2011 | Mazur et al. |
| 2011/0144645 A1 | 6/2011 | Saravia et al. |
| 2011/0178520 A1 | 7/2011 | Taylor et al. |
| 2011/0190832 A1 | 8/2011 | Taylor et al. |
| 2011/0218585 A1 | 9/2011 | Krinke et al. |
| 2011/0218626 A1 | 9/2011 | Krinke et al. |
| 2011/0282346 A1 | 11/2011 | Pham et al. |
| 2011/0282347 A1 | 11/2011 | Gordon et al. |
| 2011/0295255 A1 | 12/2011 | Roberts et al. |
| 2012/0065638 A1 | 3/2012 | Moore |
| 2012/0232533 A1 | 9/2012 | Veldman et al. |
| 2012/0239038 A1 | 9/2012 | Saravia et al. |
| 2013/0006245 A1 | 1/2013 | Stoneburner et al. |
| 2013/0012942 A1* | 1/2013 | Nelson ............... A61B 17/7208 606/63 |
| 2013/0116693 A1 | 5/2013 | Nelson et al. |
| 2015/0202413 A1 | 7/2015 | Lappin |
| 2016/0089189 A1 | 3/2016 | Buscaglia et al. |

FOREIGN PATENT DOCUMENTS

| | | |
|---|---|---|
| EP | 1815813 | 8/2007 |
| WO | WO 97/18769 | 5/1997 |
| WO | WO 98/27876 | 7/1998 |
| WO | WO 98/56301 | 12/1998 |
| WO | WO 99/20195 | 4/1999 |
| WO | WO 00/28906 | 5/2000 |

(56) References Cited

FOREIGN PATENT DOCUMENTS

| WO | WO 01/28443 | 4/2001 |
| --- | --- | --- |
| WO | WO 02/00270 | 1/2002 |
| WO | WO 02/00275 | 1/2002 |
| WO | WO 02/02158 | 1/2002 |
| WO | WO 2005/112804 | 12/2005 |
| WO | WO 2006/053210 | 5/2006 |
| WO | WO 2007/009123 | 1/2007 |
| WO | WO 2008/116175 | 9/2008 |
| WO | WO 2009/143374 | 11/2009 |
| WO | WO 2013/063145 | 5/2013 |

OTHER PUBLICATIONS

Andermahr et al., "Anatomy of the clavicle and the intramedullary nailing of midclavicular fractures," Clinical Anatomy, vol. 20; pp. 48-56; 2007.

U.S. Appl. No. 11/383,269, Minimally Invasive Actuable Bone Fixation Devices, filed May 15, 2006.

U.S. Appl. No. 11/565,534, Minimally Invasive Actuable Bone Fixation Devices, filed Nov. 30, 2006.

U.S. Appl. No. 11/383,279, Methods of Using Minimally Invasive Actuable Bone Fixation Devices, filed May 15, 2006.

U.S. Appl. No. 11/944,366, Fracture Fixation Device, Tools and Methods, filed Nov. 21, 2007.

U.S. Appl. No. 12/482,388, Fracture Fixation Device, Tools and Methods, filed Jun. 10, 2009.

U.S. Appl. No. 12/482,406, Fracture Fixation Device, Tools and Methods, filed Jun. 10, 2009.

U.S. Appl. No. 13/032,437, Fracture Fixation Device, Tools and Methods, filed Feb. 22, 2011.

U.S. Appl. No. 12/345,451, Segmented Intramedullary System and Apparatus, filed Dec. 29, 2008.

U.S. Appl. No. 12/052,919, Segmented Intramedullary Structure, filed Mar. 21, 2008.

U.S. Appl. No. 13/610,686, Segmented Intramedullary Structure, filed Sep. 11, 2012.

U.S. Appl. No. 13/861,315, Fracture Fixation Device, Tools and Methods, filed Apr. 11, 2013.

U.S. Appl. No. 13/203,713, Bone Fixation Device, Tools and Methods, filed Aug. 26, 2009.

U.S. Appl. No. 12/642,648, Bone Fixation Device, Tools and Methods, filed Dec. 18, 2009.

U.S. Appl. No. 13/147,789, Proximal Femur Fixation Apparatus, Systems and Methods With Angled Elongate Elements, filed Aug. 2, 2011.

U.S. Appl. No. 13/321,516, Snap and Twist Segmented Intramedullary System, Apparatus and Associated Methods, filed Nov. 18, 2011.

U.S. Appl. No. 13/615,078, Straight Intramedullary Fracture Fixation Devices and Methods, filed Sep. 13, 2012.

U.S. Appl. No. 13/614,523, Segmented Intramedullary Fracture Fixation Devices and Methods, filed Sep. 13, 2012.

U.S. Appl. No. 14/590,732, Dual Tip Guide Wire, filed Jan. 1, 2015.

\* cited by examiner

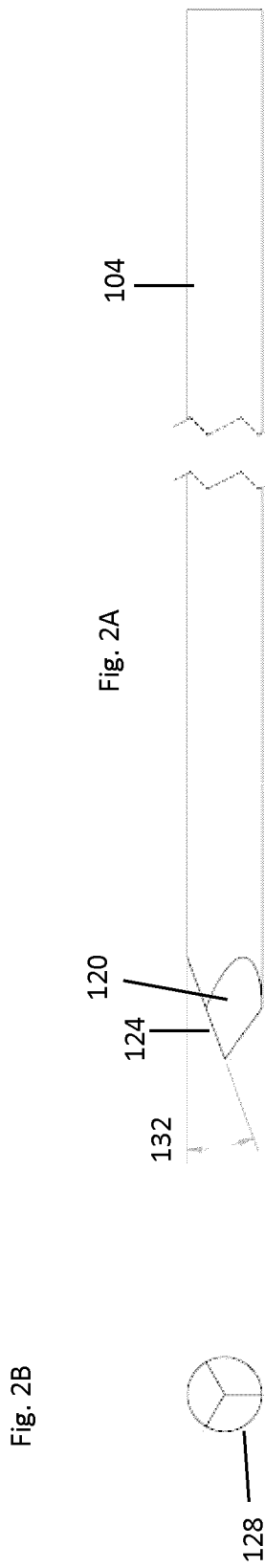

DUAL TIP GUIDE WIRE

INCORPORATION BY REFERENCE TO ANY PRIORITY APPLICATIONS

This application claims the benefit of priority from U.S. Provisional Patent Application No. 61/928,792 filed Jan. 17, 2014, which is incorporated by reference in its entirety herein. Any and all applications for which a foreign or domestic priority claim is identified in the Application Data Sheet as filed with the present application are hereby incorporated by reference under 37 CFR 1.57.

BACKGROUND OF THE INVENTION

Field

The present application relates to guide wires, and more particularly to a guide wire having a dual tip design and methods for using the guide wire.

Description of the Related Art

In the field of surgery, particularly minimally invasive surgery, it is desirable to minimize surgical steps and provide efficient procedures. Further, it is desirable to provide simpler, more intuitive tools. Further it is desirable to reduce the number of tools and surgical incisions for certain surgeries.

There is a need for a simple and robust dual tip guide wire that allows the piercing and boring of bone.

SUMMARY OF THE INVENTION

The advantages of embodiments of the dual tip guide wire of the present invention over the prior art include that the guide wire is a simple, intuitive tool. The tool advantageously has few parts, making it robust and cost-effective to manufacture.

The guide wire can be used in a variety of surgeries, such minimally invasive surgery. Further, the guide wire can be used for relatively simple cases. For instance, in various embodiments, the guide wire can be used in all surgeries, and in particular embodiments, the guide wire is favorable in surgeries involving long bones with intramedullary canals.

Particularly in the area of minimally invasive surgery, it is often desirable for the bone to be prepared in a variety of ways. For instance, a sharpened tip can pierce the bone. Alternatively, a spade tip can be rotated to bore a hole into the bone. Throughout the surgery, especially minimally invasive surgery, it is desirable to provide a tool that is capable of both piercing and boring the bone. For instance, the user may adjust the technique of hole formation depending on the location of the guide wire.

In one embodiment for minimally invasive surgery, the guide wire may be manipulated without removal from the surgical field. For instance, the user may select between piercing the bone and boring a radial diameter through the bone without removing the guide wire from the bone. The user would need fewer tools to carry out the procedure. Further, fewer tools would need to be inserted into the body, lessening the chance for infection, cross-contamination, and lost articles.

In accordance with one embodiment, a guide wire can have an elongate shaft extending along a longitudinal axis, between a first end and a second end. In some embodiments, the first end of the guide wire is sharpened. In some embodiments the guide wire includes an attachment member. The attachment member can comprise at least one flute. In some embodiments, the flutes extend along the longitudinal axis of the attachment member. The attachment member can be coupled to the second end. In some embodiments, the attachment member is laser welded to the second end of the guide wire.

In accordance with another embodiment, a method of manufacturing a guide wire is provided. The method can include the step of providing a guide wire having an elongate shaft extending along a longitudinal axis, between a first end and a second end. The method can include providing an attachment member including at least one flute. In some embodiments, the method includes the step of coupling the attachment member to the second end.

In another embodiment, a method of using a guide wire is provided. In some embodiments, the guide wire has an elongate shaft extending along a longitudinal axis, between a first end and a second end. The first end of the guide wire can be inserted into the bone, in a first direction. The second end is inserted into the bone in a second direction, wherein the first direction is substantially opposite the second direction.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 2A is a side view of the sharpened tip of the guide wire of FIG. 1;

FIG. 2B is a front view of the sharpened tip of the guide wire of FIG. 1.

DETAILED DESCRIPTION

Figure 1:
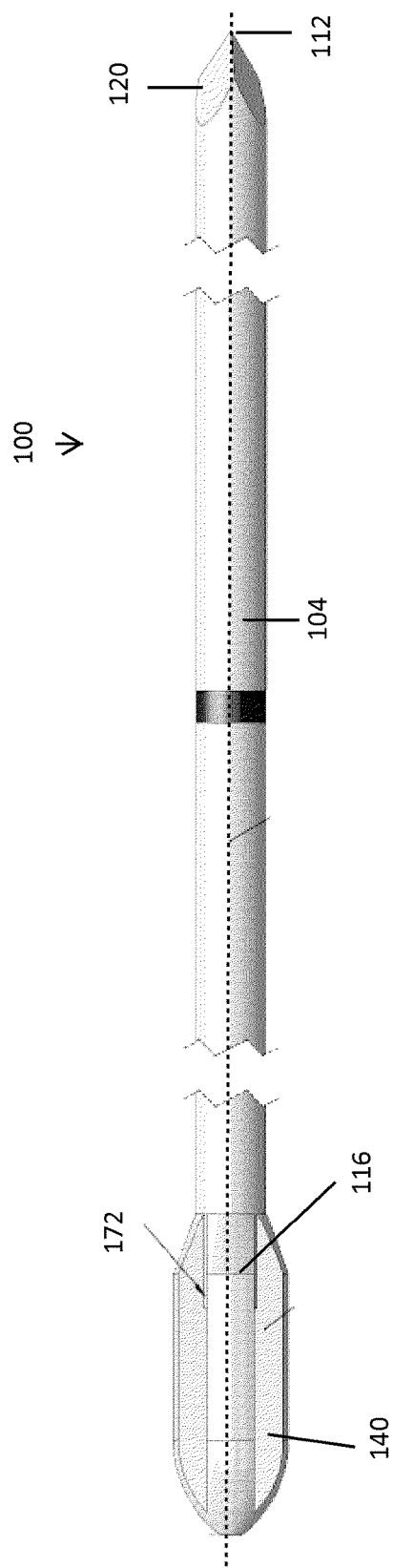
FIG. 1 is a perspective view of an embodiment of a guide wire.

FIGS. 1-4B depict an embodiment of a guide wire 100. The guide wire 100 comprises an elongate shaft 104. The elongate shaft 104 includes a longitudinal axis 108 that extends along the length of the guide wire 100. The elongate shaft 104 has a first end 112 and a second end 116.

In various embodiments, the elongate shaft 104 can comprise a medical grade biomaterial. In various embodiment, the elongate shaft 104 can comprise a metal. For instance, the elongate shaft 104 can comprise 304 Stainless Steel. In various embodiments, the elongate shaft 104 can have a diameter in the range of 0.0425 cm to 0.0435 cm, and in some embodiments, 0.0430 cm. In various embodiments, the diameter is 0.01-0.5 cm, 0.01, 0.02, 0.03, 0.04, 0.05, 0.06, 0.07, 0.08, 0.09, 0.10, 0.25 cm, or any diameter in the range(s) therein. Larger diameter guide wires are possible, for instance to perform surgery on larger or harder bones.

As shown in FIGS. 1, 2A and 2B, the first end 112 is depicted as including a sharpened tip 120. The sharpened tip 120 can be formed from flattened cuts 124 extended from the circumference 128 of the elongate shaft 104. In some embodiments, three flattened cuts 124 are formed. The three flattened cuts 124 span the circumference 128 of the elongate shaft 104 between 115 degrees to 125 degrees. In some embodiments, the three flattened cuts 124 are equidistant and each cut spans 120 degrees of the circumference 128 of the elongate shaft 104. As shown in FIG. 2A, the three flattened cuts 124 form an angle 132 with the circumference 128 of the elongate shaft 104. In some embodiments, angle 132 is between 15 degrees and 25 degrees, and in some embodiments the angle is 20 degrees. In various embodiment, the angle is between 1 and 60 degrees, 5, 10, 15, 20, 25, 30, 35, 40, 45, 50, 55 degrees, or any range therein. In some embodiments, the length L of the elongate shaft is measured from the sharpened tip 120 to the second end 116. The length L can be 19.75 cm to 22.25 cm, and in some embodiments, 22 cm. In various embodiments, the length can be 1-100 cm, 10-50 cm, 5, 15, 16, 17, 18, 19, 20, 21, 22, 23, 24, 25, 30, 35, 40, 45, 50 or more cm, or any range therein.

In various embodiment, the number, shape, and placement of the flattened cuts 124 can be modified and are presently contemplated. The flattened cuts 124 can be selected to pierce through a bone, such as a clavicle, radius, ulna, tibia, fibula, femur, or other bone. The angle 132 and the material of the guide wire 100 can contribute to the ability of the sharpened tip 120 to perform this function. The sharpened tip 120 can be configured to pierce through bone, by applying a force to the elongate shaft 104, as described below.

The sharpened tip 120 is shown as a unitary part of elongate shaft 104. Such unitary construction may make the sharpened tip more robust and durable, while reducing the cost to manufacture. Alternatively, a first attachment member 136 may be provided (not shown). The first attachment member 136 can include a sharpened tip, similar to sharpened tip 120. The first attachment member 136 may be coupled to the first end 112 of the elongate shaft 104 by any means known in the art. In some embodiments, the first attachment member 136 is laser welded to the elongate shaft 104.

The second end 116 can be cylindrical, and in some embodiments, have the same outer diameter as the elongate shaft 104. The second end 116 can have a face that is perpendicular to the longitudinal axis 108 of the elongate shaft 104.

The guide wire 100 can include a second attachment member 140 for attachment to the second end 116 of the elongate shaft 104. The second attachment member 140 can comprise a proximal end 144 and a distal end 148. The second attachment member can comprise a longitudinal axis 150 that extends from the proximal end 144 to the distal end 148. The second attachment member 140 can be generally cylindrical. The outer diameter of the second attachment member 140 can be 0.066 cm to 0.076 cm, and in some embodiments, 0.071 cm. In various embodiment, the outer diameter can be 0.01-0.25 cm, 0.02, 0.03, 0.04, 0.05, 0.06, 0.07, 0.08, 0.09, 0.1 cm or any range therein. The second attachment member 140 can be generally symmetrical.

Figure 3A:
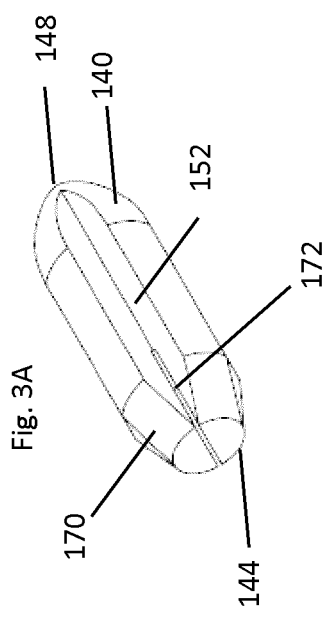
FIG. 3A is a perspective side view of the attachment member of the guide wire of FIG. 1.
Figure 3C:
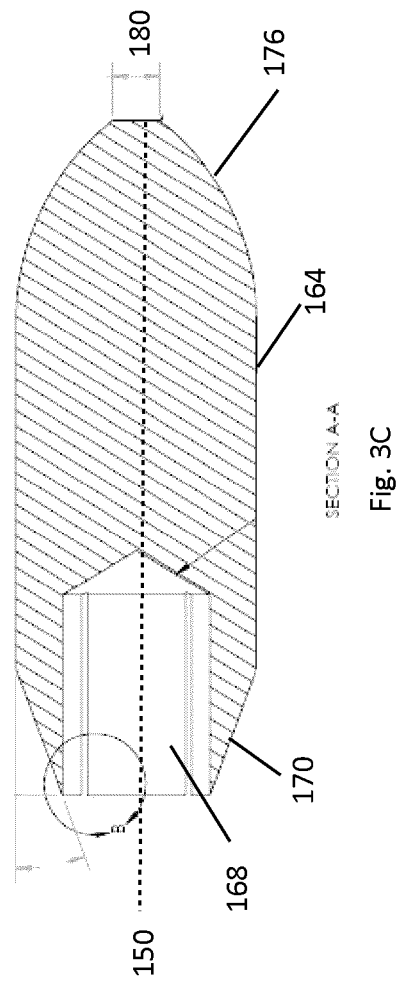
FIG. 3C is cross-sectional side view of the attachment member of FIG. 3B along section A-A.
Figure 3D:
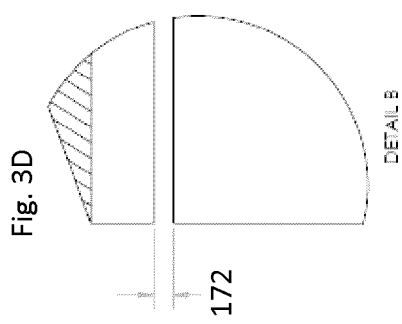
FIG. 3D is cross-sectional side view of the attachment member of FIG. 3C of detail B.
Figure 3B:
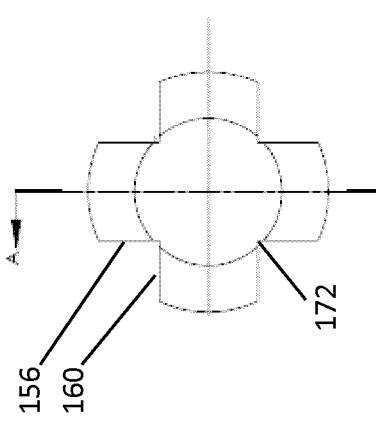
FIG. 3B is a front view of the attachment member of FIG. 3A.
Figures 4A, 4B:
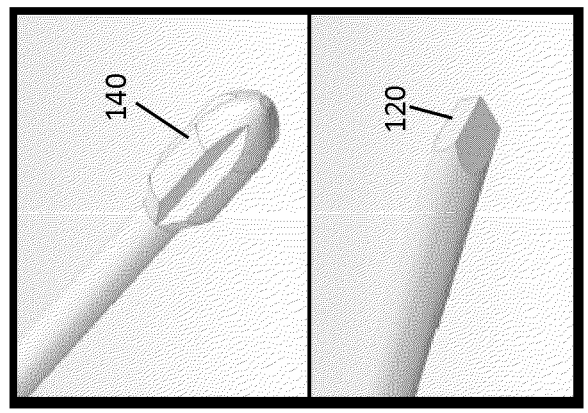
FIG. 4A is a perspective view of the attachment member of the guide wire of FIG. 1.
FIG. 4B is a perspective view of the sharpened tip of the guide wire of FIG. 1.

In some embodiments, one or more flutes 152 can extend along the longitudinal axis 150 of the second attachment member 140. Four flutes 152 are depicted but more or less flutes can be provided. Each flute 152 can be formed from two perpendicular cuts 156, 160, as shown in FIG. 3B. The perpendicular cuts 156, 160 can be sharpened or otherwise prepared. The two perpendicular cuts 156, 160 of the flutes 152 create a surface or edge which can cut cancellous bone and bore a channel within the bone. The cancellous bone is found at the end of the long bones, or the epiphysis, and inside the cortex of flat bones. The cancellous bone consists of a network of interconnecting trabecular plates and rods and is the major site of bone remodeling and resorption for mineral homeostasis. The second attachment member 140 can be rotated or oscillated to cause the flutes 152 to bore a hole in the cancellous bone.

The flutes 152 can extend over a portion of the length of the second attachment member 140 or over the entire length of the second attachment member 140. In some embodiments, the second attachment member 140 has a middle portion 164. The middle portion 164 can have a constant diameter and can be generally cylindrical. The four flutes 152 divide the middle portion 164 into four sections. The width of the sections can be between 0.028 cm and 0.030 cm, and in some embodiments, 0.029 cm. In various embodiment, the width is 0.01-0.2 cm, 0.015, 0.02, 0.025, 0.035, 0.04, 0.05, 0.75, 0.1 cm or any range therein. The second attachment member 140 resembles a spade tip.

Each section of the middle portion 164 can have the general shape of two flat edges caused by the perpendicular cuts 156, 160, a rounded external edge, and a rounded internal edge caused by a first aperture 168, described below. The rounded external edge of the middle portion 164 prevents the second attachment member 140 from cutting into the cortical bone. Cortical bone forms the shaft, or diaphysis, of long bones and the outer shell of flat bones. The cortical bone provides the main mechanical and protective function.

The proximal end 144 of the second attachment member 140 can include flattened cuts 170. The flattened cuts 170 can extend from the middle portion 164 to the proximal end 144. The flattened cuts 170 form an angle with the circumference of the middle portion 164. In some embodiments, this angle is 20 degrees. In various embodiment, the angle is 5-60 degrees, 10, 15, 25, 30, 35, 40, 45, 50, 55 degrees or any range therein. The flattened cuts 170 can provide a gentle lead-in from the elongate shaft 104.

The second attachment member 140 can comprise the first aperture 168. The first aperture 168 extends into the second attachment member 140 from the proximal end 144. The first aperture 168 extends along the longitudinal axis 150 of the second attachment member 140. In some embodiments, the first aperture 168 is formed by drilling the second attachment member 140. In some embodiments, the first aperture 168 is generally cylindrical. The first aperture 168 can include a tapered portion caused by the shape of the drill bit.

In some embodiments, the first aperture 168 extends into the flutes 152. In other words, the perpendicular cuts 156, 160 enter the first aperture 168, as shown in FIGS. 3A-3D. This overlap between the first aperture 168 and the perpendicular cuts 156, 160 forms four slots 172, as shown in FIG. 3A. In one embodiment, the slots 172 can have a width of 0.002 cm. In various embodiments, the widths can be 0.001-0.09 cm or any width therein. As shown, the slots 172 can extend along a length of the second attachment member 140 from the proximal end 144.

The first aperture 168 is sized to accept the second end 116 of the elongate shaft 104, as shown in FIG. 1. In some embodiments, the first aperture 168 has a diameter equal to the diameter of the elongate shaft 104. For instance, the first aperture 168 can have a diameter of 0.0435 cm to 0.044 cm. In various embodiments, the diameter is 0.01-0.9 cm, or any amount therein. The slots 172 allow for the elongate shaft 104 to be welded to the second attachment member 140. In other words, welding material can be used to fill slots 172 to bond the elongate shaft 104 to the second attachment member 140. In various embodiment, the attachment of components can involve welding, bonding, adhering, lock and key, mechanical interfaces, or other connecting methods.

Referring back to FIGS. 3A-3D, the distal end 148 of the second attachment member 140 can be rounded. This rounded section 176 can extend from the middle portion 164 to the distal end 148. The rounded section 176 can have a radius of 0.075 cm, or any range of radii +/−0.5 cm. The rounded section can include a flattened distal section 180. The flattened distal section 180 can have a diameter of 0.014 cm, or any range of diameters +/−0.1 cm. The overall length of the second attachment member 140 can be 0.20 cm, of which 0.06 cm can be the rounded section 176 and 0.038 cm can be the flattened cuts 170. The rounded section 176 provides a blunt end of the second attachment member 140. The second attachment member 140 can bend around the curvature of the bone and create an anatomically matching channel within the bone. The rounded section 176 can permit the second attachment member 140 to be pulled through a pin driver.

In some embodiments of the present invention, the manufacturer supplies the guide wire 100 to an end user, such as a medical professional. The manufacturer can follow a method of manufacturing the guide wire 100 which may include one or more of the following steps. The manufacturer can produce or acquire the elongate shaft 104. The manufacturer can select the material for the elongate shaft 104 based on properties including flexibility, strength, cost, availability, and biocompatibility. The manufacturer can select the diameter and length of the elongate shaft 104 based on the selected use of the user.

The manufacturer can produce the sharpened tip 120 on the first end 112 of the elongate shaft 104. In some embodiments, the manufacturer forms flattened cuts 124 which extended from the circumference 128 of the elongate shaft 104. The manufacturer can produce or acquire the first attachment member 136. The manufacturer can create sharpened tip on the end of the first attachment member 136. The manufacturer can couple the first attachment member 136 to the elongate shaft 104, using any process known in the art.

The manufacturer can produce or acquire the second attachment member 140 for attachment to the second end 116 of the elongate shaft 104. The manufacturer can create flutes 152 that can extend along the longitudinal axis 150 of the second attachment member 140. In some embodiments, each flute 152 is formed from two perpendicular cuts 156, 160 into the second attachment member 140, or by any technique known in the art. The manufacturer can create the first aperture 168 which extends into the second attachment member 140. The manufacturer can create one or more slots 172 extending between the flutes 152 and the first aperture 168. The manufacturer can couple the second attachment member 140 to the elongate shaft 104, using any process known in the art. In some embodiments, the second attachment member 140 is welded to the elongate shaft 104 via the slots 172.

A method of using the guide wire 100 can include a plurality of steps, in addition to the method of manufacturing the guide wire 100 described above. The surgeon may select one or more of the plurality of steps. Further, a manufacturer providing the guide wire 100 can provide instructions for one or more of the plurality of steps.

Figure 5:
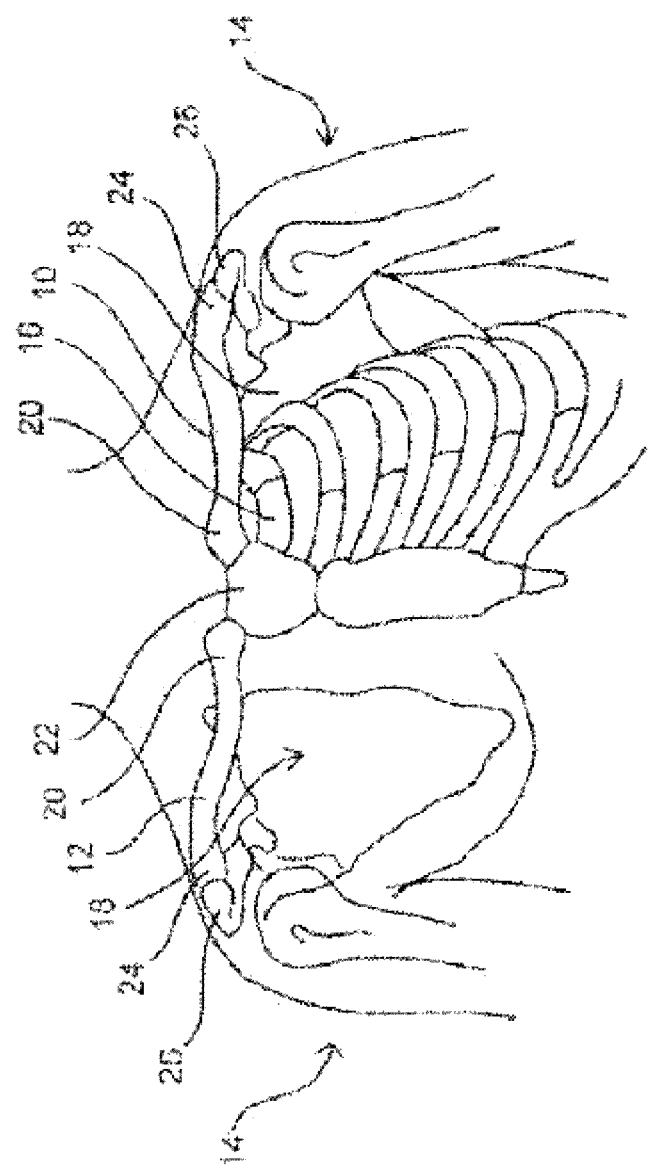
FIG. 5 is a view of the skeletal system of the pectoral girdles.

In some embodiments, the guide wire 100 is utilized to repair a fractured clavicle. FIG. 5 shows the location of the left clavicle 10 and right clavicle 12 in the human anatomy. The clavicle is classified as a membranous bone that makes up part of the pectoral girdles 14. The clavicle receives its name from the Latin claviculam, meaning "little key", because the bone rotates along its axis like a key when the shoulder is abducted. This movement is palpable with the opposite hand. The clavicle is a doubly curved short bone that connects the arm (upper limb) to the body (trunk), located directly above the first rib 16. It acts as a shunt to keep the scapula 18 in position so the arm can hang freely. At its medial end 20, the clavicle 10, 12 articulates with the manubrium of the sternum 22 (breast-bone) at the sternoclavicular joint. At its lateral end 24, the clavicle 10, 12 articulates with the acromion 26 of the scapula (shoulder blade) at the acromioclavicular joint. As mentioned, the clavicle is a double curved bone, comprising a lateral segment having a lateral curve and a medial segment having a medical curve. It has been found by Jonas Andermahr et al. in "Anatomy of the clavicle and the Intramedullary Nailing of Midclavicular Fractures" (Clinical Anatomy 20 (2007): 48-56), that the medial curve radius is about 7.1.+/−1.3 cm overall (N=196) with women (N=106) having a slightly smaller curvature of 7.0.+/−1.2 cm and men (N=90) having a slightly larger curvature of 7.3.+/−1.3 cm. The lateral curve radius is about 3.9.+/−1.4 cm overall (N=196) with women (N=106) having a slightly larger curvature of 4.2.+/−1.6 cm and men (N=90) having a slightly smaller curvature of 3.6.+/−1.1 cm.

Figure 6:
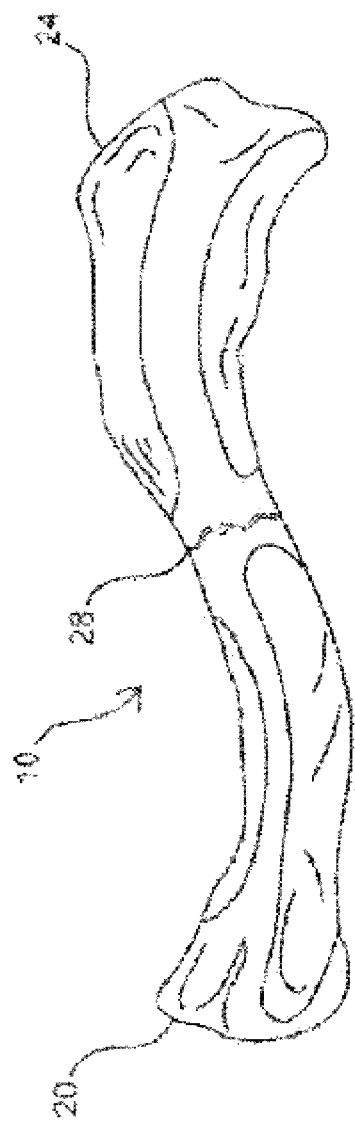
FIG. 6 is a view of the superior surface of a left clavicle.

FIG. 6 is an enlarged view of the superior surface of the left clavicle 10. As can be seen, the clavicle 10 has a rounded medial end (sternal extremity) 20 and a flattened lateral end (acromial extremity) 24. From the roughly pyramidal sternal end 20, clavicle 10 curves laterally and posteriorly for roughly half its length. It then forms a smooth posterior curve to articulate with a process of the scapula (acromion), as described above. The flat, acromial end 24 of the clavicle 10 is broader than the sternal end 20. The acromial end 24 has a rough inferior surface that bears prominent lines and tubercles. These surface features are attachment sites for muscles and ligaments of the shoulder. The clavicle is made up of spongy (cancellous) bone with a shell of compact bone. It is a dermal bone derived from elements originally attached to the skull. An exemplary mid-shaft fracture site 28 is depicted in FIG. 6.

In one embodiment, a method of using the guide wire 100 comprises selecting a preferred guide wire 100 based on characteristics of the guide wire. For example, the surgeon may select the guide wire based on the length or diameter of the elongate shaft 104, the sharpened tip 120 or the first attachment member 136, the diameter of the second attachment member 140, the flutes 152 and/or any other feature of the guide wire 100 described above. The selection of the guide wire 100 may be directed by the surgical procedure to be done. The selection can also be guided by the type of bone encountered. The manufacturer may provide a variety of guide wires 100 from which the surgeon can select.

An incision can be made at the fracture 28, and tissue is retracted if needed to access the fracture. Fracture 28 can be then distracted to gain access to the medial end of the lateral segment of the bone.

The surgeon or other practitioner can drill a pilot hole into the body. In some embodiment, the drill has a drill bit of 2 mm, which forms a pilot hole having a diameter of 2 mm. The pilot hole can correspond with the longitudinal axis of a bone. In some embodiments, the bone is the clavicle, or collarbone. The longitudinal axis of the bone can be substantially straight, such as a femur, or curved, such as a clavicle. The pilot hole can be drilled in the medial segment. The pilot hole can be drilled in the lateral segment. The pilot hole can be drilled in the medial segment and the lateral segment, in any order.

The surgeon or other practitioner aligns the sharpened tip 120 with the pilot hole. The sharpened tip 120 enters the pilot hole at fracture 28. The first location can be on the lateral segment. The sharpened tip 120, and associated guide wire 100, can be pushed manually or with the assistance of a tool toward the second location, toward the lateral end 24. The sharpened tip 120 pierces through the bone as the guide wire 100 is pushed. In some embodiments, the elongate shaft 104 is pushed in order to advance the sharpened tip 120. In some embodiments, a force is applied to the second attachment member 140 in order to advance the sharpened tip 120.

The surgeon may use a drill guide to facilitate insertion of the sharpened tip 120 within the bone. A guiding sheath or cannulated drill bit may alternatively be used to facilitate the placement of the guide wire 100 from anterior to posterior in the lateral clavicle fragment, thereby allowing the guide wire 100 to be passed either anterior to posterior in the lateral fragment or posterior to anterior in the lateral fragment. The sharpened tip 120 may be extended along the longitudinal axis of a bone to the surface of the lateral end 24.

Depending on the needs of the surgery, the surgeon may tent the skin of the patient away from the bone or organs, for instance. The surgeon can make an incision, which can be a lateral incision. From this incision, the surgeon can manipulate the guide wire 100. The guide wire 100 can be moved by applying a force, for instance a push force, from the fracture 28. The guide wire 100 can be manipulated by applying a force from the lateral incision. This force can be a pull force depending on the desired location of the guide wire 100.

Figure 12A:
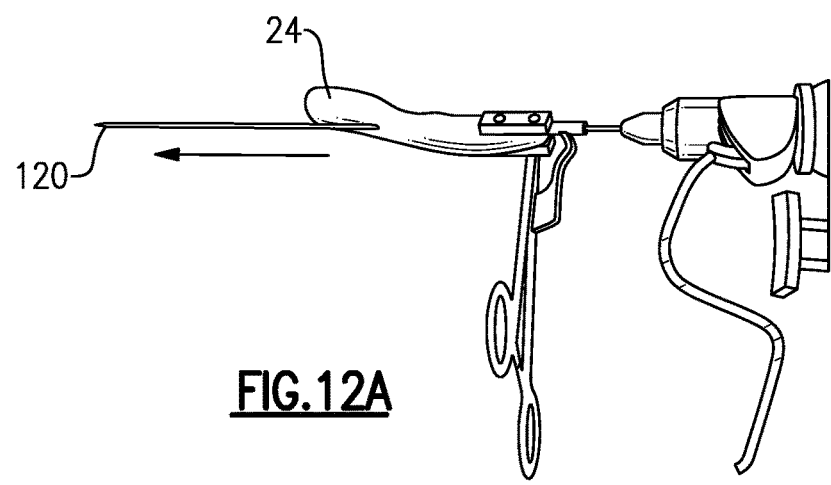
FIG. 12A is an image of a method step.
Figure 12B:
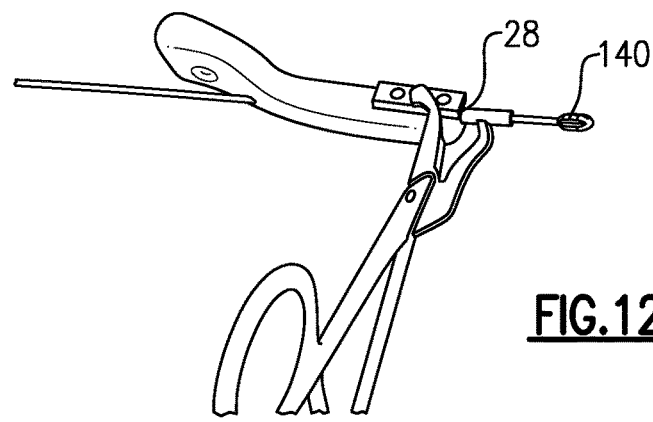
FIG. 12B is an image of a method step.

The surgeon can create a path through the bone corresponding to the diameter of the sharpened tip 120. As the guide wire 100 is advance, the path in the bone is enlarged to the diameter of the second attachment member 140. The flattened cuts 170 extend from the proximal end 144 of the second attachment member 140. The flattened cuts 170 may facilitate the enlargement of the path created by the sharpened tip 120, due to the angle of the flattened cuts 170. FIGS. 12 A-C show the lateral segment of the bone with lateral end 24. The medial segment is omitted for clarity. Driving the guide wire 100 and sharpened tip 120 into the lateral segment is shown in FIG. 12A.

Based on the shape of the guide wire 100, the second attachment member 140 will follow the sharpened tip 120. For instance, when the sharpened tip 120 is moved from the fracture 28 toward the lateral end 24, the attachment member 140 will similarly traverse toward the lateral end. The attachment member 140 may remain external to the lateral bone segment as the sharpened tip 120 is moved toward the lateral end 24. The sharpened tip 120 is advance away from the fracture 28 toward the lateral end 24. This is considered moving the guide wire 100 in a first direction.

The guide wire 100 is manipulated until the second attachment member 140 is at the fracture 28. The second attachment member 140 is shown at the fracture site in FIG. 12B. This manipulation may involve pulling or pushing the sharpened tip 120 beyond and away from the fracture site. At this point in the surgery, the sharpened tip 120 and elongate shaft 140 can be within the lateral segment of the bone.

The surgeon can reduce the fracture, by any known technique in the art. With the fracture approximated, the guide wire 100 may be advanced across the fracture 28 and into the medial portion of clavicle 12. In particular, the second attachment member 140 can be advanced into the medial segment of the bone. The second attachment member 140 leads. In other words, the sharpened tip 120 will follow the second attachment member 140.

Figure 12C:
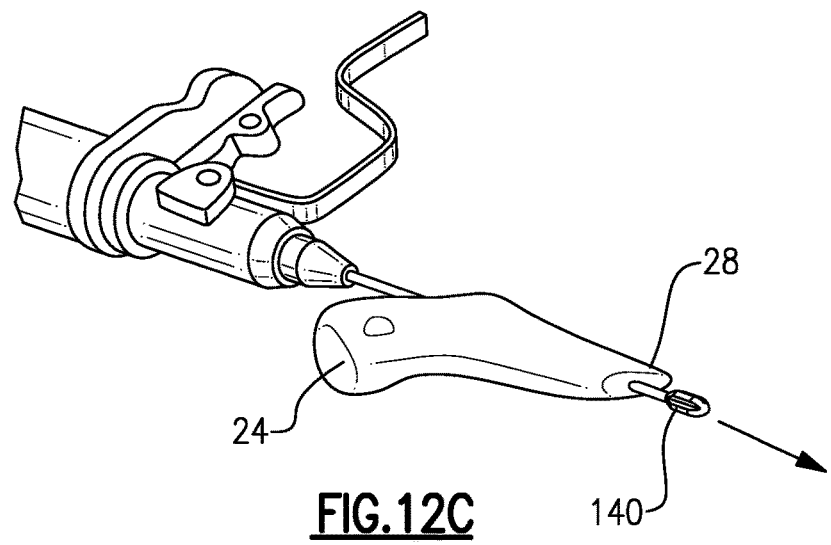
FIG. 12 C is an image of a method step.

The guide wire 100 can be oscillated or rotated in order to advance the second attachment member 140 from the lateral segment into the medial segment. The flutes 152 create a boring surface for the second attachment member. The oscillation motion causes the second attachment member to create a channel in the medial segment of the bone. Note that the path of the guide wire 100 may need to bend to approximately follow the longitudinal axis of clavicle 12. The second attachment member 140 is advance away from the fracture 28 toward the medial end 20. Advancing the second attachment member into the medial segment is shown in FIG. 12C. This is considered moving the guide wire 100 in a second direction. The first direction can be opposite or substantially opposite the second direction.

The guide wire 100 can be described as a bi-directional guide wire. The surgeon can move the guide wire 100 in a first direction to advance the sharpened tip 120. The surgeon can pierce the bone. The surgeon can move the guide wire 100 in a second direction to advance the second attachment member 140. The surgeon can oscillate or rotate the second attachment member 140. The second attachment member 140 can bore a hole in the cancellous bone by rotation of the flutes 152. The second attachment member 140 can bend around the curvature of the clavicle and create a curved channel within the bone.

A cannulated reaming tool or drill bit or other channel forming instrument may then be advanced over the guide wire 100 to create a straight or curved channel in the medial portion of clavicle 12 as needed. The desired intramedullary channel is created on both sides of fracture 28. The cannulated tool may be stiff or flexible. For example, if the tool is flexible, it may be advanced over the guide wire and follow the curve of the channel to create a contoured and anatomically matching channel. The cannulated tool may also function as a sheath or trocar-like device. For example, the cannulated tool may remain at least partially within the bone. Alternatively, the guide wire may be removed, and a tool (cannulated or not) may be moved through the bone independently.

Figure 7:
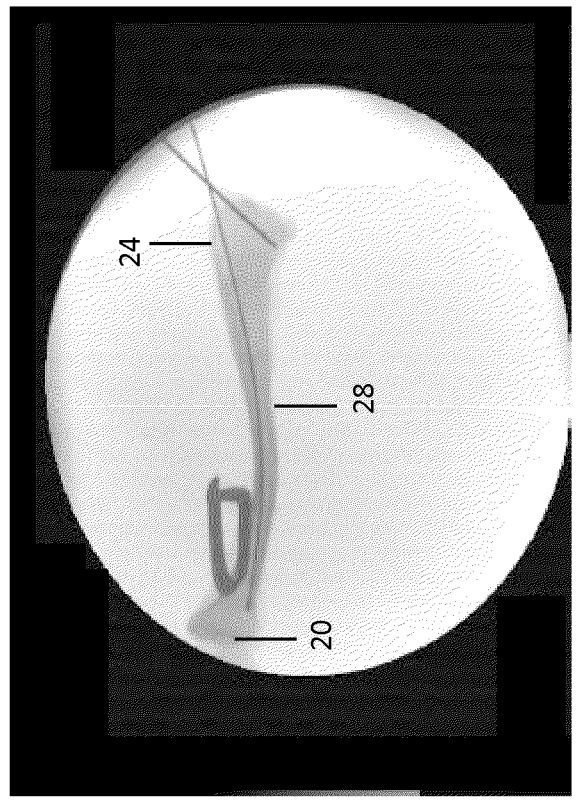
FIG. 7 is an image of the guide wire of FIG. 1 inserted into a bone.
Figure 8:
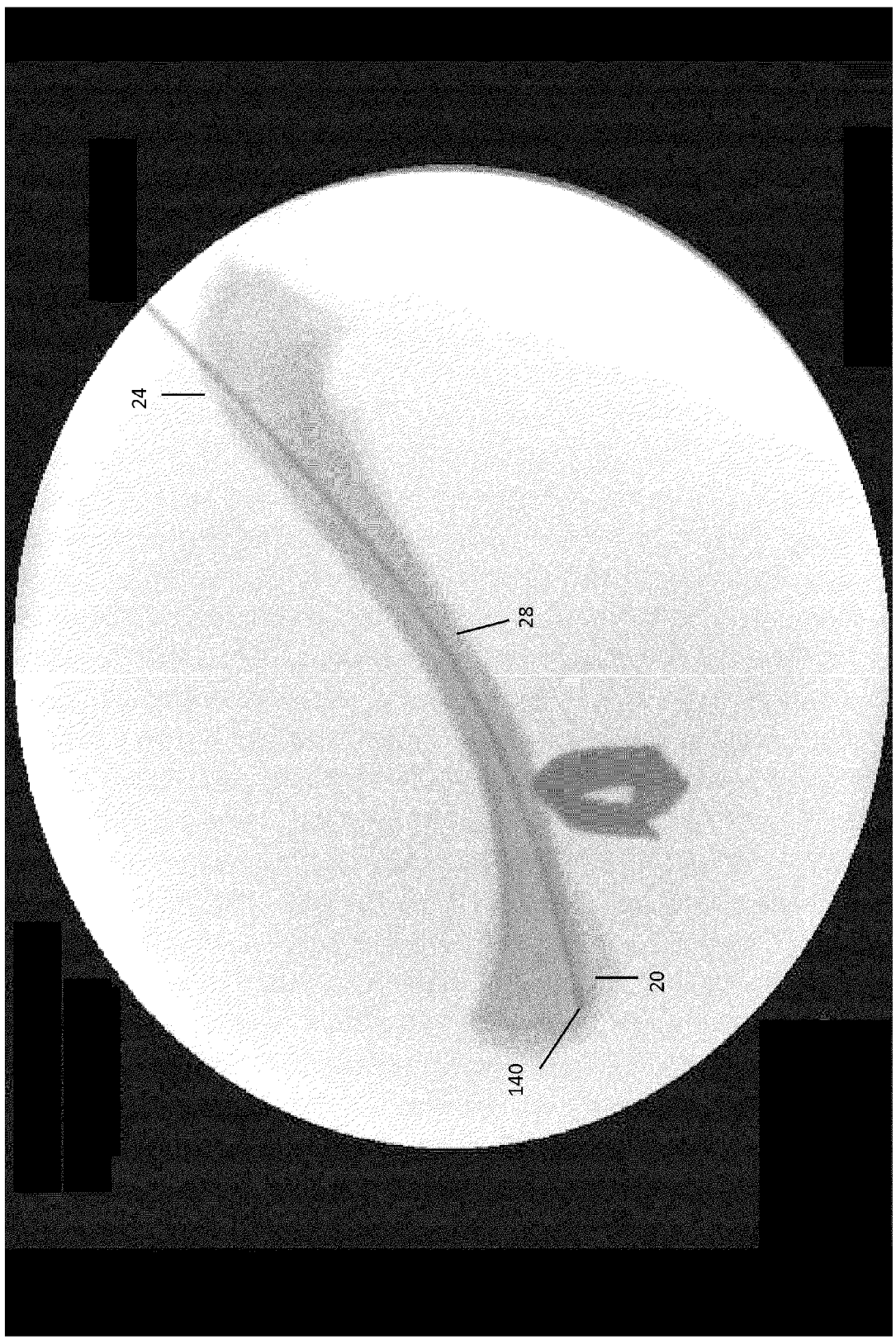
FIG. 8 is an image of the guide wire of FIG. 1 inserted into a bone.
Figure 9:
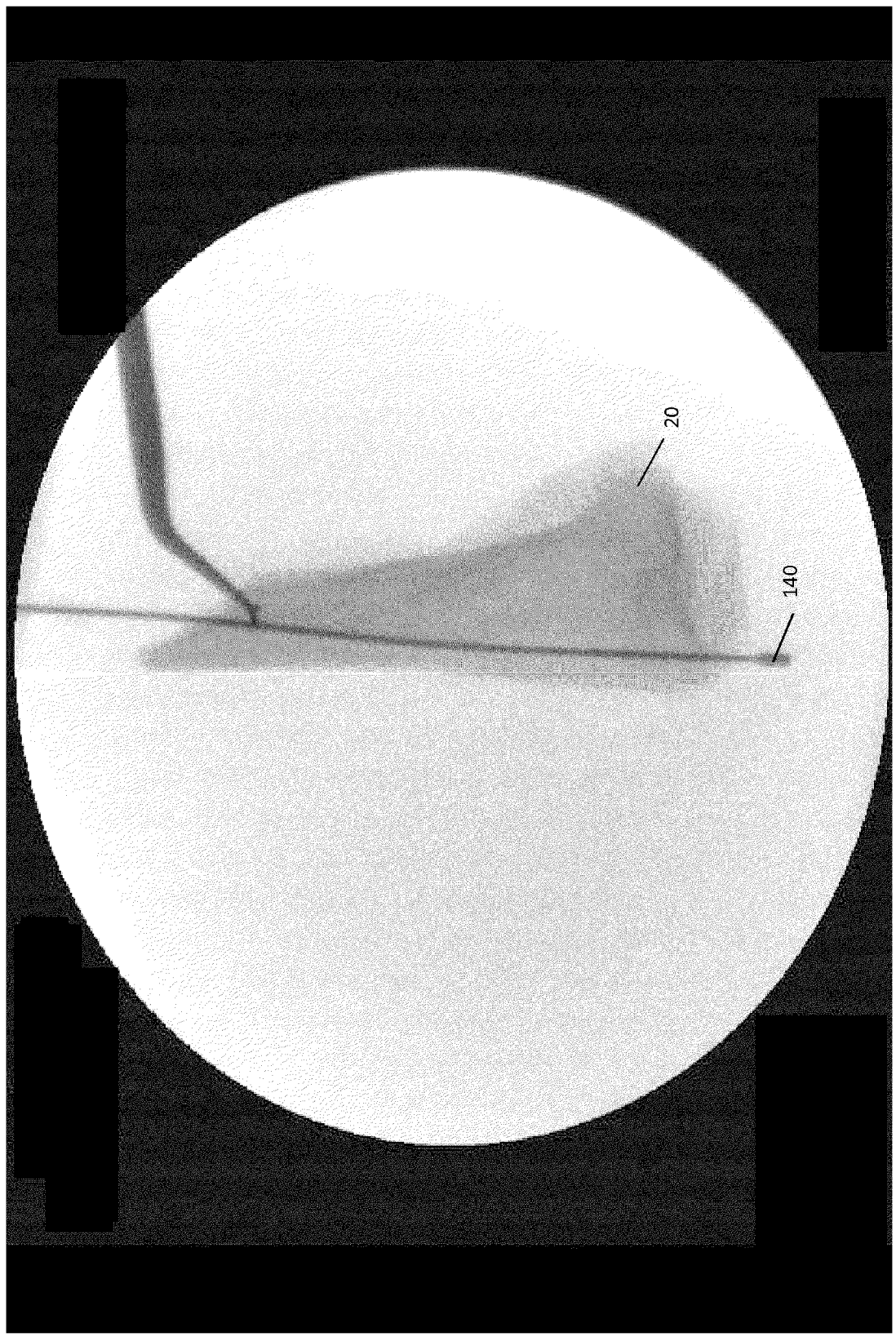
FIG. 9 is an image of the guide wire of FIG. 1 inserted into a bone.
Figure 10:
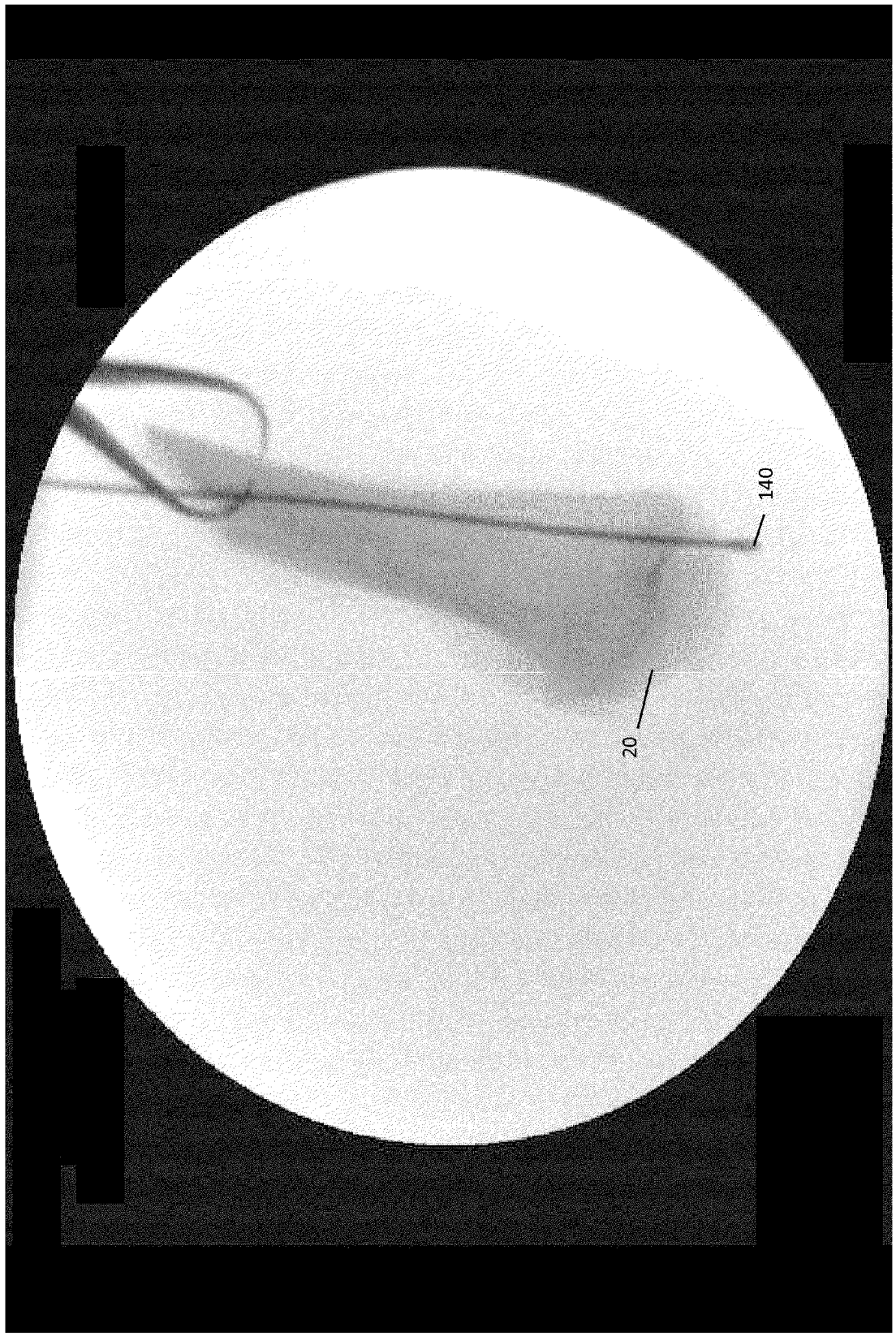
FIG. 10 is an image of the guide wire of FIG. 1 inserted into a bone.
Figure 11:
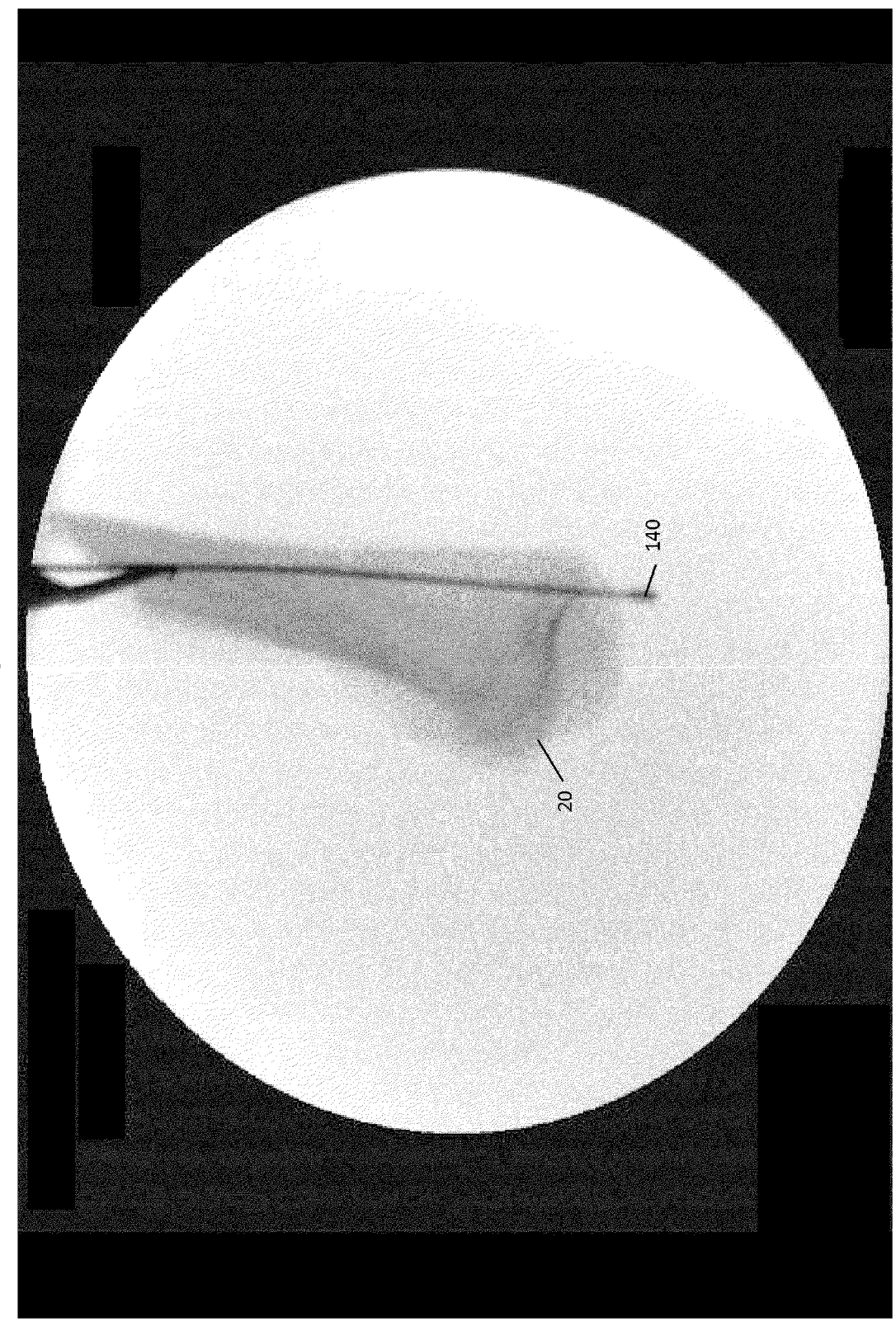
FIG. 11 is an image of the guide wire of FIG. 1 inserted into a bone.

FIGS. 7-11 show device 100 implanted in a right clavicle 12. FIGS. 7-8 shows clavicle 12 from a superior perspective, while FIG. 9-11 shows clavicle 12 from a posterior perspective. As shown, the clavicle has a lateral segment having a lateral end 24 and a medial segment having a medial end 20. In a patient, the lateral end is adjacent to the acromion of a scapula and the medial end is adjacent to the manubrium of a sternum. As shown in FIGS. 7-11, the lateral segment is between the fracture 28 and the lateral end 24 and the medial segment is between the fracture and the medial end 20. The figures show the second attachment member 140 after boring through the medial segment of the bone.

The procedure may be done under fluoroscopy or other imaging technique to allow the surgeon to visualize the path of the guide wire 100 as it is advanced, and/or to confirm its location once extended through clavicle 12.

In some embodiments of utilizing guide wire 100, a bone fixation device is inserted into the channel through a lateral exit point. The channel may be created such that the channel traverses the fracture 28 of the bone and comprises at least one segment that substantially follows the anatomical contour of the bone. The cannulated tool may be used to expand the diameter of the channel to a diameter large enough to accept the fixation device. The bone fixation device may be inserted into the channel such that the device transverses the fracture. Exemplary bone fixation devices are described in commonly owned U.S. Publications 2013/0116693 filed 13 Sep. 2013 and 2013/0012942 filed 13 Sep. 2013, which are incorporated by reference herein in their entirety.

In an alternative method, the entire implant procedure may be performed through a single incision at the lateral end 24 of clavicle 12. In this alternative procedure, the sharpened end 120 of the guide wire 100 enters the lateral portion of clavicle 12 and is advanced to fracture site 28.

Once the guide wire is inserted in the lateral portion of the bone, the channel may be created in a clavicle bone by inserting a tool or a series of tools through the incision and into the end portion of the lateral segment of the clavicle. As described above, a tool is inserted into the bone and advanced through the bone. The tool may have a stiffness such that it may traverse bone without bending.

The guide wire 100 and/or tool is removed from the lateral portion of the clavicle through the single incision. The guide wire 100 is rotated 180 degrees. The second attachment member 140 of the guide wire 100 enters the lateral portion of clavicle 12 and is advanced to fracture site 28. In other words, the guide wire 100 may be inserted such that the second attachment member 140 is driven into the clavicle at the lateral end and moved through the bone. In some embodiments, the guide wire 100 is advanced in the channel created by the tool A guide wire 100 may then be advanced across the approximated fracture site 28 and into the medial portion of the bone. The second attachment member 140 is blunt and can bend around the curvature of the clavicle and create an anatomically matching (i.e. curved) channel within the bone. This shape does not penetrate cortical bone, but rather bends around the curvature of the bone. The second attachment member 140 may be inserted to create the medial segment of the channel. The channel within the medial segment of the clavicle substantially follows the anatomical curvature or contour of the clavicle bone. The guide wire 100 may be oscillated to advance the second attachment member 140 into the medial segment.

A cannulated drill or reamer may then be advanced over the guide wire to complete the intramedullary channel in the medial portion of clavicle 12. For example, a tool with adequate stiffness to traverse the fracture may be one that is stiff enough to maintain a substantially straight trajectory through the midline of the bone, and one that will not buckle or otherwise bend or fail within the bone or across the fracture. This alternative method may be referred to as a "closed" procedure and requires more work and skill to perform, but is less invasive than the first method described.

Any suitable combination of tools may be used to create the channels in both the medial segment and the lateral segment of the clavicle. The tools may include hand tools or power tools. The tools may also include awls, drill bits, guide wires, or any other suitable tools to create a channel within bone. The awls may be curved awls, straight awls, and/or malleable awls (i.e. the user may change the radius of curvature of the awl intraoperatively). The tools may have any suitable head geometry such as a pointed geometry, a blunted geometry, a fluted geometry, etc. In some cases, a blunted tip is preferably over a sharp tip as to avoid important nerves (such as the bracheoplexus) and vessels (such as the subclavian artery which supplies blood to the brain) that surround the clavicle bone. The tools may be cannulated (i.e. hollow) or solid. In the case that the tool is cannulated, it may be adapted to be inserted into the bone over a guide wire and/or the tool may function as a sheath or trocar like device and a guide wire may be inserted through the cannula of the cannulated tool.

The segments may be prepared in any suitable order. As an example, the medial segment may be prepared first. The channel is created in the medial segment by inserting a tool into the medial segment starting at the fractured end. The tool is then moved through the medial segment creating the channel. The channel substantially follows the anatomical contour of the bone. In the case of the clavicle, this means following the curve of the bone through the medial segment. A curved tool may be used to create the curved or contoured segment of the channel. A straight tool may be used to create the substantially straight segments before and/or after the curved or contoured segment. The channel can be created substantially along the midline of the bone. Furthermore, the channel may run deeper into the medial segment of the bone than conventional channels can because it is a curved channel. Conventional channels cannot be curved, and therefore they cannot be created past the curved portion or bend in the medial segment of the clavicle bone without breaking out of the bone.

Additional tools may be inserted into the channel over the guide wire. For example, a depth gauge may be inserted into the channel. In some embodiments, the depth gauge includes markings to indicate the depth of the channel created. The markings may be reverse scale markings such that the deeper that the gauge can be inserted into the channel, the higher the marking that will be legible. The depth reading may be used to determine the length of device needed to fit correctly within the channel. Various lengths and diameters of devices may be provided for the surgeon to select from to suit the particular anatomy and fracture involved. Dimensions and configurations can be altered for use in bones other than the clavicle.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. For example, the prosthetic joint and locking mechanism described herein can be incorporated into other prosthetic joints, such as a prosthetic hip joint, a prosthetic elbow joint, a prosthetic shoulder joint, etc. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A method of using a guide wire comprising:
   positioning a guide wire having an elongate shaft extending along a longitudinal axis, the guide wire having a first end and a second end, wherein the first end of the guide wire is sharpened and the second end of the guide wire comprises at least one straight flute that extends parallel to the longitudinal axis;
   inserting the first end of the guide wire into a clavicle in a first direction; and
   after inserting the first end of the guide wire, inserting the second end of the guide wire into the clavicle in a second direction, wherein the first direction is substantially opposite the second direction.

2. The method of claim 1, further comprising cutting cancellous bone with the second end of the guide wire by oscillating the guidewire.

3. The method of claim 1, further comprising boring a channel within the bone with the second end of the guide wire.

4. The method of claim 1, further comprising rotating the second end of the guide wire to cause the at least one flute to bore a hole in the bone.

5. The method of claim 1, further comprising making an incision at a fracture.

6. The method of claim 1, wherein the second end of the guide wire comprises an attachment member.

7. The method of claim 6, wherein the at least one flute comprises a slot configured to facilitate coupling the attachment member to the elongate shaft.

8. The method of claim 6, wherein the attachment member has a larger diameter than the elongate shaft.

9. A method of using a guide wire comprising:
   positioning a guide wire near a bone, the guide wire comprising an elongate shaft extending along a longitudinal axis, the guide wire comprising a first end and a second end, wherein the first end of the guide wire is sharpened and the second end of the guide wire comprises at least one longitudinal flute, the bone comprising a fracture;
   inserting the first end of the guide wire into the bone in a first direction; and
   oscillating the second end of the guide wire into the bone in a second direction such that the at least one longitudinal flute bores a channel into the bone.

10. The method of claim 9, further comprising distracting the fracture.

11. The method of claim 9, wherein inserting the first end of the guide wire into the bone comprises pushing the guide wire toward an end of the bone.

12. The method of claim 9, further comprising drilling a pilot hole before inserting the first end of the guide wire into the bone.

13. The method of claim 9, further comprising reducing the fracture.

14. The method of claim 9, further comprising moving the guide wire until the second end of the guide wire is at the fracture while the first end of the guide wire is within the bone.

15. The method of claim 9, further comprising cutting cancellous bone with the second end of the guide wire while the first end of the guide wire is within the bone.

16. A method of using a guide wire comprising:
   providing a guide wire comprising an elongate shaft extending along a longitudinal axis, the guide wire comprising a first end and a second end, wherein an attachment member is located at the second end of the guide wire, the attachment member comprising two longitudinal flutes extending on opposite sides of the attachment member;
   inserting the first end of the guide wire into a first bone portion in a first direction; and
   inserting the second end of the guide wire into a second bone portion in a second direction, wherein the first direction is substantially opposite the second direction.

17. The method of claim 16, further comprising moving the guide wire until the second end of the guide wire is at a fracture while the first end of the guide wire is within the first bone portion.

18. The method of claim 16, further comprising cutting cancellous bone with the second end of the guide wire while the first end of the guide wire is within the first bone portion.

19. The method of claim 16, wherein at least one longitudinal flute comprises a slot configured to allow the attachment member to be welded to the elongate shaft.

20. The method of claim 9, wherein the guidewire is configured to flex along the length of the guidewire when inserting the first end of the guide wire into the first bone portion.

* * * * *